United States Patent
Lynn et al.

(10) Patent No.: US 10,557,044 B2
(45) Date of Patent: Feb. 11, 2020

(54) SLIPPERY ANTI-FOULING SURFACES FABRICATED FROM REACTIVE POLYMER MULTILAYERS

(71) Applicant: Wisconsin Alumni Research Foundation, Madison, WI (US)

(72) Inventors: David Lynn, Middleton, WI (US); Uttam Manna, Madison, WI (US); Matthew Carter, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 404 days.

(21) Appl. No.: 15/192,425

(22) Filed: Jun. 24, 2016

(65) Prior Publication Data

US 2017/0022371 A1    Jan. 26, 2017

Related U.S. Application Data

(60) Provisional application No. 62/184,219, filed on Jun. 24, 2015.

(51) Int. Cl.
  *G01N 13/00* (2006.01)
  *C09D 5/16* (2006.01)

(52) U.S. Cl.
  CPC .......... *C09D 5/1625* (2013.01); *C09D 5/1668* (2013.01); *G01N 13/00* (2013.01)

(58) Field of Classification Search
  CPC ..... C09D 5/1625; C09D 5/1668; G01N 13/00
  See application file for complete search history.

(56) References Cited

U.S. PATENT DOCUMENTS

| | | | |
|---|---|---|---|
| 7,642,285 B2 | 1/2010 | Blackwell et al. | |
| 7,910,622 B2 | 3/2011 | Blackwell et al. | |
| 8,071,210 B2 | 12/2011 | Lynn et al. | |
| 8,269,024 B2 | 9/2012 | Blackwell et al. | |
| 8,367,680 B2 | 2/2013 | Blackwell et al. | |
| 8,624,063 B2 | 1/2014 | Blackwell et al. | |
| 8,815,943 B2 | 8/2014 | Blackwell et al. | |
| 2011/0306142 A1* | 12/2011 | Lynn | G01N 21/21 436/85 |
| 2017/0022372 A1 | 1/2017 | Lynn et al. | |

OTHER PUBLICATIONS

Allen et al. (Mar. 14, 2014) "Targeting virulence: can we make evolution-proof drugs?" Nat. Rev. Microbiol. 12:300-308.
Antipov et al. (2001) "Sustained Release Properties of Polyelectrolyte Multilayer Capsules," J. Phys. Chem. B. 105:2281-2284.

(Continued)

*Primary Examiner* — Victor S Chang
(74) *Attorney, Agent, or Firm* — Leydig, Voit & Mayer, Ltd.

(57) ABSTRACT

This invention provides slippery liquid-infused porous surfaces (SLIPS) using nanoporous or microporous and chemically reactive polymer multilayers. This approach permits fabrication of slippery anti-fouling coatings on complex surfaces and provides new means to manipulate the mobilities of contacting aqueous fluids. The results expand the range of tools that can be used to manipulate the behaviors of SLIPS and open the door to new applications of this emerging class of soft materials.

32 Claims, 17 Drawing Sheets

(56) References Cited

OTHER PUBLICATIONS

Arciola et al. (2012) "Biofilm formation in *Staphylococcus* implant infections. A review of molecular mechanisms and implications for biofilm-resistant materials," Biomaterials. 33:5967-5982.

Bae et al. (Dec. 18, 2013) "25th Anniversary Article: Scalable Multiscale Patterned Structures Inspired by Nature: The Role of Hierarchy," Adv. Mater. 26:675-700.

Bai et al. (2011) "Recent Advances in Colloidal and Interfacial Phenomena Involving Liquid Crystals," Langmuir. 27:5719-5738.

Banerjee et al. (2011) "Antifouling Coatings: Recent Developments in the Design of Surfaces That Prevent Fouling by Proteins, Bacteria, and Marine Organisms," Adv. Mater. 23:690-718.

Barthlott et al. (1997) "Purity of the sacred lotus, or escape from contamination in biological surfaces," Planta. 202:1-8.

Bassler et al. (2006) "Bacterially speaking," Cell. 125:237-246.

Bellanger et al. (Jan. 9, 2014) "Chemical and Physical Pathways for the Preparation of Superoleophobic Surfaces and Related Wetting Theories," Chem. Rev. 114:2694-2716.

Bhargava et al. (1996) "Triclosan: applications and safety," Am. J. Infect. Control. 24:209-218.

Bortleson et al. (1972) "Recent sedimentary history of Lake Mendota, Wis," Environ. Sci. Technol. 6:799-808.

Boudou et al. (2010) "Multiple functionalities of polyelectrolyte multilayer films: new biomedical applications," Adv. Mater. 22:441-467.

Brake et al. (2003) "Biomolecular interactions at phospholipid-decorated surfaces of liquid crystals," Science. 302:2094-2097.

Breitbach et al. (2011) "Surface-mediated release of a synthetic small-molecule modulator of bacterial quorum sensing: Gradual release enhances activity," Chem. Comm. 47:370-372.

Brock et al. (1984) "Significance of algal excretory products for growth of epilimnetic bacteria," Appl. Environ. Microbiol. 47:731-734.

Broderick et al. (2012) "Covalent Layer-by-Layer Assembly of Water-Permeable and Water-Impermeable Polymer Multilayers on Highly Water-Soluble and Water-Sensitive Substrates," Chem. Mater. 24:1786-1795.

Broderick et al. (2012) "In situ Synthesis of Oligonucleotide Arrays on Surfaces Coated with Crosslinked Polymer Multilayers," Chem. Mater. 24:938-945.

Broderick et al. (Jan. 20, 2013) "Surface-mediated release of a small-molecule modulator of bacterial biofilm formation: A non-bactericidal approach to inhibiting biofilm formation in Pseudomonas aeruginosa," Adv. Healthcare Mater. 2:993-1000.

Broderick et al. (Jun. 28, 2014) "Surface coatings that promote rapid release of peptide-based AgrC inhibitors for attenuation of quorum sensing in *Staphylococcus aureus*," Adv. Healthcare Mater. 3:97-105.

Buck et al. (2007) "Layer-by-layer assembly of reactive ultrathin films mediated by click-type reactions of poly(2-alkenyl azlactone)s," Adv. Mater. 19:3951-3955.

Buck et al. (2009) "Chemical Modification of Reactive Multilayered Films Fabricated from Poly(2-alkenyl azlactone)s: Design of Surfaces that Prevent or Promote Mammalian Cell Adhesion and Bacterial Biofilm Growth," Biomacromolecules. 10:1564-1574.

Buck et al. (2010) "Functionalization of Fibers Using Azlactone-Containing Polymers: Layer-by-Layer Fabrication of Reactive Thin Films on the Surfaces of Hair and Cellulose-Based Materials," ACS Appl. Mater. Interfaces. 2:1421-1429.

Buck et al. (2010) "Superhydrophobic thin films fabricated by reactive layer-by-layer assembly of azlactone-functionalized polymers," Chem. Mater. 22:6319-6327.

Buck et al. (Oct. 12, 2011) "Azlactone-functionalized polymers as reactive platforms for the design of advanced materials: Progress in the last ten years," Polym. Chem. 3:66-80.

Busscher et al. (2012) "Biomaterial-associated infection: Locating the finish line in the race for the surface," Sci. Transl. Med. 4:153rv110.

Cai et al. (2014) "Filefish-Inspired Surface Design for Anisotropic Underwater Oleophobicity," Adv. Funct. Mater. 24(6):809-816.

Camilli et al. (2006) "Bacterial small-molecule signaling pathways," Science. 311:1113-1116.

Campoccia et al. (Aug. 15, 2013) "A review of the biomaterials technologies for infection-resistant surfaces," Biomaterials. 34:8533-8554.

Cassie et al. (1944) "Wettability of porous surfaces," Trans. Faraday Soc. 40:546-551.

Chapman et al. (2000) "Surveying for Surfaces that Resist the Adsorption of Proteins," J. Am. Chem. Soc. 122:8303-8304.

Chu et al. (Jan. 31, 2014) "Superamphiphobic surfaces," Chem. Soc. Rev. 43:2784-2798.

Chung et al. (2002) "Methods of Loading and Releasing Low Molecular Weight Cationic Molecules in Weak Polyelectrolyte Multilayer Films," Langmuir. 18:1176-1183.

Clatworthy et al. (2007) "Targeting virulence: a new paradigm for antimicrobial therapy," Nat. Chem. Biol. 3:541-548.

Costerton et al. (1999) "Bacterial biofilms: A common cause of persistent infections," Science. 284:1318-1322.

Daniel et al. (Jun. 2013) "Lubricant-infused micro/nano-structured surfaces with tunable dynamic omniphobicity at high temperatures," Appl. Phys. Lett. 102:231603.

De Kievit et al. (2001) "Quorum-sensing genes in Pseudomonas aeruginosa biofilms: their role and expression patterns," Appl. Environ. Microbiol. 67:1865-1873.

Deng et al. (2010) "Laundering Durability of Superhydrophobic Cotton Fabric," Adv. Mater. 22:5473-5477.

Deng et al. (2011) "Transparent, Thermally Stable and Mechanically Robust Superhydrophobic Surfaces Made from Porous Silica Capsules," Adv. Mater. 23:2962-2965.

Deng et al. (2012) "Candle soot as a template for a transparent robust superamphiphobic coating," Science. 335:67-70.

Eibergen et al. (Oct. 13, 2015) "Potent and selective modulation of the RhlR quorum sensing receptor by using non-native ligands: An emerging target for virulence control in Pseudomonas aeruginosa," ChemBioChem. 16(16):2348-2356.

Epstein et al. (2012) "Liquid-infused structured surfaces with exceptional anti-biofouling performance," Proc. Natl. Acad. Sci. USA. 109:13182-13187.

Feng et al. (2002) "Super-Hydrophobic Surfaces: From Natural to Artificial," Adv. Mater. 14:1857-1860.

Frei et al. (2012) "2-Aminobenzimidazole derivatives strongly inhibit and disperse Pseudomonas aeruginosa biofilms," Angew. Chem. Int. Ed. 51:5226-5229.

Gao et al. (2004) "Biophysics: Water-repellent legs of water striders," Nature. 432:36.

Genzer et al. (2000) "Creating long-lived superhydrophobic polymer surfaces through mechanically assembled monolayers," Science. 290:2130-2133.

Geske et al. (2008) "Comparative analyses of N-acylated homoserine Lactones reveal unique structural features that dictate their ability to activate or inhibit quorum sensing," ChemBioChem. 9:389-400.

Geske et al. (2008) "Evaluation of a focused library of N-aryl L-homoserine lactones reveals a new set of potent quorum sensing modulators," Bioorg. Med. Chem. Lett. 18:5978-5981.

Glavan et al. (Jul. 26, 2013) "Omniphobic 'RF Paper' Produced by Silanization of Paper with Fluoroalkyltrichlorosilanes," Adv. Funct. Mater. 24:60-70.

Grinthal et al. (Oct. 14, 2013) "Mobile interfaces: Liquids as a perfect structural material for multifunctional, antifouling surfaces," Chem. Mater. 26:698-708.

Heilmann et al. (1984) "Chemistry of alkenyl azlactones. I. Radiation-sensitive materials derived from azlactone-containing copolymers," J. Polym. Sci. Part A. 22(5):1179-1186.

Heilmann et al. (1998) "The chemistry of 2-alkenyl-5(4H)-oxazolones. VIII acid-catalyzed reaction with alcohols," Tetrahedron. 54(40):12151-12160.

Heilmann et al. (2001) "Chemistry and technology of 2-alkenyl azlactones," J. Polymer Sci. Part A. 39(21):3655-3677.

Holloway (1955) "Genetic recombination in Pseudomonas aeruginosa," J. Gen. Microbiol. 13:572-581.

Howell et al. (Feb. 4, 2015) "Stability of Surface-Immobilized Lubricant Interfaces under Flow," Chem. Mater. 27:1792-1800.

(56) References Cited

OTHER PUBLICATIONS

Howell et al. (Jul. 23, 2014) "Self-Replenishing Vascularized Fouling-Release Surfaces," ACS Appl. Mater. Inter. 6:13299-13307.
Huang et al. (2011) "Controllable Underwater Oil-Adhesion-Interface Films Assembled from Nonspherical Particles," Adv. Funct. Mater. 21:4436-4441.
Huang et al. (Sep. 4, 2013) "Omniphobic slippery coatings based on lubricant-infused porous polyelectrolyte multilayers," ACS Macro Lett. 2:826-829.
Ionov et al. (2012) "Self-healing superhydrophobic materials," Phys. Chem. Chem. Phys. 14:10497-10502.
Jewell et al. (2008) "Multilayered polyelectrolyte assemblies as platforms for the delivery of DNA and other nucleic acid-based therapeutics," Adv. Drug Deliver. Rev. 60:979-999.
Ji et al. (2006) "Fabrication of a Superhydrophobic Surface from the Amplified Exponential Growth of a Multilayer," Adv. Mater. 18:1441-1444.
Jin et al. (2011) "Underwater Oil Capture by a Three-Dimensional Network Architectured Organosilane Surface," Adv. Mater. 23:2861-2864.
Jisr et al. (2005) "Hydrophobic and Ultrahydrophobic Multilayer Thin Films from Perfluorinated Polyelectrolytes," Angew. Chem. Int. Ed. 44:782-785.
Johnston et al. (2007) "Assembling DNA into Advanced Materials: From Nanostructured Films to Biosensing and Delivery Systems," Adv. Mater. 19 :3727-3730.
Jones et al. (2000) "Triclosan: A review of effectiveness and safety in health care settings," Am. J. Infect. Control. 28:184-196.
Jung et al. (2009) "Wetting Behavior of Water and Oil Droplets in Three-Phase Interfaces for Hydrophobicity/philicity and Oleophobicity/philicity," Langmuir. 25:14165-14173.
Kharlampieva et al. (2004) "Release of a Dye from Hydrogen-Bonded and Electrostatically Assembled Polymer Films Triggered by Adsorption of a Polyelectrolyte," Langmuir. 20:9677-9685.
Kim et al. (2012) "Liquid-Infused Nanostructured Surfaces with Extreme Anti-Ice and Anti-Frost Performance," ACS Nano. 6:6569-6577.
Kim et al. (2013) "Hierarchical or Not? Effect of the Length Scale and Hierarchy of the Surface Roughness on Omniphobicity of Lubricant-Infused Substrates," Nano Lett. 13:1793-1799.
Kim et al. (2008) "Hydrogen-Bonding Layer-by-Layer-Assembled Biodegradable Polymeric Micelles as Drug Delivery Vehicles from Surfaces," ACS Nano. 2:386-392.
Kojic et al. (2004) "Candida infections of medical devices," Clin. Microbiol. Rev. 17:255-267.
Kool et al. (Nov. 12, 2013) "Fast Hydrazone Reactants: Electronic and Acid/Base Effects Strongly Influence Rate at Biological pH," Journal of the American Chemical Society. 135(47):17663-17666.
Kota et al. (2012) "Hygro-responsive membranes for effective oil-water separation," Nat. Commun. 3:1025.
Kratochvil et al. (Aug. 26, 2015) "Nanoporous superhydrophobic coatings that promote the extended release of water-labile quorum sensing inhibitors and enable long-term modulation of quorum sensing in *Staphylococcus aureus*," ACS Biomater. Sci. Eng. 1:1039-1049.
Leslie et al. (Oct. 12, 2014) "A bioinspired omniphobic surface coating on medical devices prevents thrombosis and biofouling," Nat. Biotechnol. 32:1134-1140.
Levkin et al. (2009) "Porous Polymer Coatings: a Versatile Approach to Superhydrophobic Surfaces," Adv. Funct. Mater. 19:1993-1998.
Li et al. (2010) "Bioinspired self-healing superhydrophobic coatings," Angew. Chem. Int. Ed. 49:6129-6133.
Li et al. (2012) "Printable Superhydrophilic—Superhydrophobic Micropatterns Based on Supported Lipid Layers," Langmuir. 28:8286-8291.
Li et al. (Dec. 18, 2014) "Reactive superhydrophobic surface and its photoinduced disulfide-ene and thiol-ene (bio)functionalization," Nano Lett. 15:675-681.

Li et al. (Jul. 5, 2013) "Hydrophobic liquid-infused porous polymer surfaces for antibacterial applications," ACS Appl. Mater. Interfaces 5:6704-6711.
Lin et al. (2010) "Bio-inspired hierarchical macromolecule-nanoclay hydrogels for robust underwater superoleophobicity," Adv. Mater. 22:4826-4830.
Lin et al. (2011) "Endotoxin-induced structural transformations in liquid crystalline droplets," Science. 332:1297-1300.
Lipinski (2000) "Drug-like properties and the causes of poor solubility and poor permeability," Journal of Pharmacological and Toxicological Methods. 44:235-249.
Liu et al. (2008) "Ultrathin Multilayered Films that Promote the Release of Two DNA Constructs with Separate and Distinct Release Profiles," Adv. Mater. 20:4148-4153.
Liu et al. (2009) "Bioinspired Design of a Superoleophobic and Low Adhesive Water/Solid Interface," Adv. Mater. 21:665-669.
Liu et al. (2010) "Recent developments in bio-inspired special wettability," Chem. Soc. Rev. 39:3240-3255.
Liu et al. (2012) "Bioinspired oil strider floating at the oil/water interface supported by huge superoleophobic force," ACS Nano. 6:5614-5620.
Liu et al. (2012) "Bio-Inspired Self-Cleaning Surfaces," Ann. Rev. Mater. Res. 42:231-263.
Liu et al. (2012) "Clam's shell inspired high-energy inorganic coatings with underwater low adhesive superoleophobicity," Adv. Mater. 24:3401-3405.
Liu et al. (2012) "Complementary effects of nanosilver and superhydrophobic coatings on the prevention of marine bacterial adhesion," ACS Appl. Mater. Interfaces. 4:4683-4690.
Liu et al. (Jun. 17, 2013) "Organogel-based thin films for self-cleaning on various surfaces," Adv. Mater. 25:4477-4481.
Lynn (2007) "Peeling Back the Layers: Controlled Erosion and Triggered Disassembly of Multilayered Polyelectrolyte Thin Films," Adv. Mater. 19:4118-4130.
Ma et al. (Feb. 11, 2014) "Substrate-Independent Underwater Superoleophobic Surfaces Inspired by Fish-Skin and Mussel-Adhesives," Adv. Mater. Interfaces. 1:1300092.
MacDonald et al. (2008) "Release of a model protein from biodegradable self assembled films for surface delivery applications," J. Control. Release. 131:228-234.
Manna et al. (2008) "Encapsulation of Uncharged Water-Insoluble Organic Substance in Polymeric Membrane Capsules via Layer-by-Layer Approach," J. Phys. Chem. B. 112:13258-13262.
Manna et al. (2012) "Chemical Patterning and Physical Refinement of Reactive Superhydrophobic Surfaces," Adv. Mater. 24:4291-4295.
Manna et al. (Apr. 27, 2016) "Slippery liquid-infused porous surfaces that prevent microbial surface fouling and kill non-adherent pathogens in surrounding media: A controlled release approach," Advanced Functional Materials. 26(21):3599-3611.
Manna et al. (Apr. 8, 2015) "Fabrication of liquid-infused surfaces using reactive polymer multilayers: Principles for manipulating the behaviors and mobilities of aqueous fluids on slippery liquid interfaces," Adv. Mater. 27:3007-3012.
Manna et al. (Aug. 13, 2013) "Restoration of Superhydrophobicity in Crushed Polymer Films by Treatment with Water: Self-Healing and Recovery of Damaged Topographic Features Aided by an Unlikely Source," Adv. Mater. 25:5104-5108.
Manna et al. (Aug. 25, 2013) "Superhydrophobic polymer multilayers that promote the extended, long-term release of embedded water-soluble agents," Adv. Mater. 25:6405-6409.
Manna et al. (Feb. 4, 2015) "Synthetic Surfaces with Robust and Tunable Underwater Superoleophobicity," Adv. Funct. Mater. 25:1672-1681.
Mattmann et al. (2011) "Potent and selective synthetic modulators of a quorum sensing repressor in Pseudomonas aeruginosa identified from second-generation libraries of N-acylated L-homoserine lactones," ChemBioChem. 12:942-949.
Mavor et al. (2005) "Systemic fungal infections caused by Candida species: epidemiology, infection process and virulence attributes," Curr. Drug Targ. 6:863-874.

(56) References Cited

OTHER PUBLICATIONS

Mellbye et al. (Dec. 27, 2013) "Physiological framework for the regulation of quorum sensing-dependent public goods in Pseudomonas aeruginosa," J. Bacteriol. 196:1155-1164.

Moore et al. (Oct. 22, 2015) "A comparative analysis of synthetic quorum sensing modulators in Pseudomonas aeruginosa: New insights into mechanism, active efflux susceptibility, phenotypic response, and next-generation ligand design," J. Am. Chem. Soc. 137:14626-14639.

Muh et al. (2006) "Novel Pseudomonas aeruginosa quorum-sensing inhibitors identified in an ultra-high-throughput screen," Antimicrob. Agents Chemother. 50:3674-3679.

Ng et al. (2009) "Bacterial quorum-sensing network architectures," Annu. Rev. Genet. 43:197-222.

Nicolle (2005) "Catheter-related urinary tract infection," Drug. Aging. 22:627-639.

Nishimoto et al. (Oct. 23, 2013) "Bioinspired self-cleaning surfaces with superhydrophobicity, superoleophobicity, and superhydrophilicity," RSC Adv. 3:671-690.

O'Reilly et al. (Nov. 2, 2015) "Structure-Based Design and Biological Evaluation of Triphenyl Scaffold-Based Hybrid Compounds as Hydrolytically Stable Modulators of a LuxR-Type Quorum Sensing Receptor," ACS Infect. Dis. 2:32-38.

O'Loughlin et al. (Oct. 29, 2013) "A quorum-sensing inhibitor blocks Pseudomonas aeruginosa virulence and biofilm formation," Proc. Natl. Acad. Sci. USA. 110:17981-17986.

Orner et al. (2004) "Arrays for the Combinatorial Exploration of Cell Adhesion," J. Am. Chem. Soc. 126:10808-10809.

Parker et al. (2001) "Water capture by a desert beetle," Nature. 414:33-34.

Passerini et al. (1992) "Biofilms on indwelling vascular catheters," Crit. Care Med. 20:665-673.

Peeters et al. (2008) "Comparison of multiple methods for quantification of microbial biofilms grown in microtiter plates," J. Microbiol. Meth. 72:157-165.

Pereira et al. (May 20, 2014) "Brønsted acid catalyzed azlactone ring opening by nucleophiles," Tetrahedron. 70(20):3271-.

Ramage et al. (2005) "Candida biofilms: an update," Eukaryot. Cell. 4:633-638.

Ramage et al. (2009) "Our current understanding of fungal biofilms," Crit. Rev. Microbiol. 35:340-355.

Rasmussen et al. (1984) "Chemistry of alkenylazlactones, 2 Reaction with thiols," Makromol. Chem. Rapid Commun. 5(2):67-70.

Schmitt et al. (Feb. 15, 2016) "Peptide Conjugation to a Polymer Coating via Native Chemical Ligation of Azlactones for Cell Culture," Biomacromolecules. 17(3):1040-1047.

Schmitt et al. (May 20, 2015) "Polyethylene Glycol Coatings on Plastic Substrates for Chemically Defined Stem Cell Culture," Adv. Healthcare Mater. 4(10):1555-1564.

Seon et al. (Nov. 18, 2015) "Polyelectrolyte Multilayers: A Versatile Tool for Preparing Antimicrobial Coatings," Langmuir. 31:12856-12872.

Shen et al. (2012) "Asymmetric free-standing film with multifunctional anti-bacterial and self-cleaning properties," ACS Appl. Mater. Interfaces. 4:4476-4483.

Smith et al. (2009) "Layer-by-layer platform technology for small-molecule delivery," Angew. Chem. Int. Ed. 48:8974-8977.

Smith et al. (Dec. 17, 2012) "Droplet mobility on lubricant-impregnated surfaces," Soft Matter. 9:1772-1780.

Soike et al. (2010) "Engineering a Material Surface for Drug Delivery and Imaging using Layer-by-Layer Assembly of Functionalized Nanoparticles," Adv. Mater. 22:1392-1397.

Stacy et al. (2012) "Attenuation of quorum sensing in the pathogen Acinetobacter baumannii using non-native N-acyl homoserine lactones," ACS Chem. Biol. 7:1719-1728.

Starkey et al. (Aug. 21, 2014) "Identification of Anti-virulence Compounds That Disrupt Quorum-Sensing Regulated Acute and Persistent Pathogenicity," PLoS Pathog. 10(8):e1004321. pp. 1-17.

Subramanyam et al. (Sep. 26, 2013) "Ice Adhesion on Lubricant-Impregnated Textured Surfaces," Langmuir. 29:13414-13418.

Sun et al. (2010) "Release of DNA from polyelectrolyte multilayers fabricated using 'charge-shifting' cationic polymers: Tunable temporal control and sequential, multi-agent release," J. Control. Release. 148:91-100.

Sunny et al. (Sep. 1, 2014) "Lubricant-infused nanoparticulate coatings assembled by layer-by-layer deposition," Adv. Funct. Mater. 24:6658-6667.

Taff et al. (2012) "Comparative analysis of Candida biofilm quantitation assays," Med. Mycology. 50:214-218.

Tian et al. (Jul. 8, 2014) "Interfacial Material System Exhibiting Superwettability," Adv. Mater. 26:6872-6897.

Timonen eet al. (Jul. 19, 2013) "Switchable Static and Dynamic Self-Assembly of Magnetic Droplets on Superhydrophobic Surfaces," Science. 341:253-257.

Tuteja et al. (2007) "Designing superoleophobic surfaces," Science. 318:1618-1622.

Ueda et al. (Jan. 23, 2013) "Emerging applications of superhydrophilic-superhydrophobic micropatterns," Adv. Mater. 25:1234-1247.

Ueda et al. (May 28, 2013) "Micropatterning hydrophobic liquid on a porous polymer surface for long-term selective cell-repellency," Adv. Healthcare Mater. 2(11):1425-1429.

Verho et al. (2011) "Mechanically Durable Superhydrophobic Surfaces," Adv. Mater. 23:673-678.

Vogel et al. (Jul. 31, 2013) "Transparency and damage tolerance of patternable omniphobic lubricated surfaces based on inverse colloidal monolayers," Nat. Commun. 4:2176.

Wei et al. (Sep. 18, 2014) "Supramolecular polymers as surface coatings: Rapid fabrication of healable superhydrophobic and slippery surfaces," Adv. Mater. 26:7358-7364.

Welsh et al. (Feb. 18, 2016) "Chemical genetics reveals environment-specific roles for quorum sensing circuits in Pseudomonas aeruginosa," Cell Chem. Biol. 23:361-369.

Welsh et al. (Jan. 9, 2015) "Small molecule disruption of quorum sensing cross-regulation in Pseudomonas aeruginosa causes major and unexpected alterations to virulence phenotypes," J. Am. Chem. Soc. 137:1510-1519.

Wenzel (1936) "Resistance of Solid Surfaces to Wetting by Water," Ind. Eng. Chem. 28:988-994.

Wong et al. (2011) "Bioinspired self-repairing slippery surfaces with pressure-stable omniphobicity," Nature. 477:443-447.

Xiao et al. (Sep. 25, 2013) "Slippery liquid-infused porous surfaces showing marine antibiofouling properties," ACS Appl. Mater. Interfaces. 5:10074-10080.

Xin et al. (2012) "Schiff's base as a stimuli-responsive linker in polymer chemistry," Polymer Chemistry. 3(11):3045-3055.

Xu et al. (May 17, 2013) "Nacre-Inspired Design of Mechanical Stable Coating with Underwater Superoleophobicity," ACS Nano. 7:5077-5083.

Xu et al. (Nov. 7, 2012) "An Ion-Induced Low-Oil-Adhesion Organic/Inorganic Hybrid Film for Stable Superoleophobicity in Seawater," Adv. Mater. 25:606-611.

Yao et al. (2011) "Applications of Bio-Inspired Special Wettable Surfaces," Adv. Mater. 23:719-734.

Yao et al. (Apr. 7, 2013) "Adaptive fluid-infused porous films with tunable transparency and wettability," Nat. Mater. 12:529-534.

Yao et al. (Dec. 17, 2013) "Temperature-Driven Switching of Water Adhesion on Organogel Surface," Adv. Mater. 26:1895-1900.

Yohe et al. (2012) "3D superhydrophobic electrospun meshes as reinforcement materials for sustained local drug delivery against colorectal cancer cells," J. Control. Release. 162:92-101.

Yohe et al. (2012) "Superhydrophobic Materials for Tunable Drug Release: Using Displacement of Air to Control Delivery Rates," J. Am. Chem. Soc. 134:2016-2019.

Yohe et al. (2013) "A Mechanistic Study of Wetting Superhydrophobic Porous 3D Meshes," Adv. Funct. Mater. 23:3628-3637.

You et al. (Sep. 4, 2014) "Fabrication of a Micro-omnifluidic Device by Omniphilic/Omniphobic Patterning on Nanostructured Surfaces," ACS Nano. 8:9016-9024.

Yuan et al. (2008) "Superwetting nanowire membranes for selective absorption," Nat. Nanotechnol. 3:332-336.

Zelikin (2010) "Drug Releasing Polymer Thin Films: New Era of Surface-Mediated Drug Delivery," ACS Nano. 4:2494-2509.

(56) References Cited

OTHER PUBLICATIONS

Zhai et al. (2004) "Stable Superhydrophobic Coatings from Polyelectrolyte Multilayers," Nano Lett. 4:1349-1353.
Zhai et al. (2006) "Patterned Superhydrophobic Surfaces: Toward a Synthetic Mimic of the Namib Desert Beetle," Nano Lett. 6:1213-1217.
Zhang et al. (Feb. 18, 2013) "Superhydrophobic and Superoleophilic PVDF Membranes for Effective Separation of Water-in-Oil Emulsions with High Flux," Adv. Mater. 25:2071-2076.
Zhang et al. (Oct. 2, 2013) "Nepenthes Pitcher Inspired Anti-Wetting Silicone Nanofilaments Coatings: Preparation, Unique Anti-Wetting and Self-Cleaning Behaviors," Adv. Funct. Mater. 24:1074-1080.

* cited by examiner

SLIPPERY ANTI-FOULING SURFACES FABRICATED FROM REACTIVE POLYMER MULTILAYERS

CROSS-REFERENCE TO RELATED APPLICATIONS

This application claims priority from U.S. Provisional Patent Application No. 62/184,219, filed Jun. 24, 2015, which is incorporated by reference herein to the extent that there is no inconsistency with the present disclosure.

STATEMENT REGARDING FEDERALLY SPONSORED RESEARCH OR DEVELOPMENT

This invention was made with government support under N00014-14-1-0791 and N00014-07-1-0255 awarded by the US Navy/ONR and 1121288 awarded by the National Science Foundation. The government has certain rights in the invention.

BACKGROUND OF THE INVENTION

Slippery liquid-infused porous surfaces (SLIPS) are an emerging class of bio-inspired soft matter that exhibits unique and robust antifouling behavior. These materials are fabricated by infusion of viscous oils into porous surfaces, yielding interfaces that allow other fluids to slide off (e.g., with sliding angles as low as 2°). This slippery behavior arises from an ability to host and maintain thin films of oil at their surfaces, placing a premium on chemical compatibility between the matrix and the oil and revealing design criteria that can be exploited to manipulate the behaviors of contacting fluids (e.g., to tune sliding angles and velocities or create responsive surfaces that allow control over these and other interfacial behaviors). Surfaces and coatings that exhibit these characteristics have enabled the design of new anti-icing surfaces, slippery containers for the dispensing of commercial liquids and gels, and new liquid-infused interfaces that are resistant to biofouling in complex aqueous, biological, and marine environments.

Aizenberg and co-workers reported the first examples of SLIPS by infusing perfluorinated liquids into nanofibrous Teflon membranes (Wong et al., Nature, 2011, 477: 443-447). Since that report, many different approaches have been used to design substrates, coat surfaces, and functionalize interfaces with combinations of porosity, roughness, and surface chemistry that lead to slippery surfaces when infused with different liquid phases. Recent reports have extended work on SLIPS on planar surfaces to develop approaches to the fabrication of SLIPS on more complex objects. These reports address challenges related to assembly, versatility, and durability that will be needed to integrate this class of liquid-infused materials in practical settings. These examples have, however, emerged only recently. The fabrication of SLIPS on complex surfaces and the development of means to tune, pattern, or manipulate the interfacial properties of these liquid-infused materials remains a challenge.

The present invention addresses the challenges related to the fabrication and functionalization of SLIPS on complex surfaces, and provides a means for tuning interfacial properties and manipulating the behaviors of fluids in contact with this emerging class of soft materials.

SUMMARY OF THE INVENTION

The present invention is directed to the design of slippery liquid-infused porous surfaces (SLIPS) and surface coatings that are based on the infusion of oils into nanoporous or microporous polymer multilayer films fabricated by "reactive" or "covalent" layer-by-layer assembly such as described in U.S. Pat. No. 8,071,210. This approach is straightforward to implement and can be used to fabricate physically and chemically durable slippery liquid-infused porous surfaces on objects of arbitrary shape, size, and topology (e.g., on objects that are curved or hollow, on surfaces that are hard or soft, and on objects that are flexible, reconfigurable, or able to be transferred to other surfaces without loss of slippery behavior).

In an embodiment, the present invention provides a slippery liquid-infused porous surfaces (SLIPS) multilayer film comprising one or more bilayers infused with an oil, wherein each bilayer comprises an optionally functionalized first polymer layer in contact with a second polymer layer, and wherein the multilayer film has a nanoscale or microscale porosity. Preferably, the multilayer film has a nanoscale porosity. The infusion of the oil into at least a portion of the rough or porous surfaces of the multilayer film causes other liquids placed in contact with the multilayer film to slide off the multilayer film or a surface coated with the multilayer film.

In another embodiment, the present invention provides a method for fabricating a slippery liquid-infused porous surface (SLIP) multilayer film on a substrate, where the multilayer film comprises one or more bilayers, the method comprising the steps of: a) exposing the surface of the substrate to a first solution comprising a first polymer wherein a layer of the first polymer is deposited on at least a portion of the substrate; b) exposing the substrate to a second solution comprising a second polymer wherein the second polymer reacts with the first polymer layer and a layer of the second polymer is deposited on at least a portion of the first polymer layer, thereby forming a bilayer having nanoscale porosity or microscale porosity in the multilayer film; and c) exposing the substrate to an oil wherein said oil coats at least a portion of the multilayer film and said oil at least partially fills the pores of at least a portion of said multilayer film. The method optionally comprises a rinsing step comprising exposing or washing the substrate with a rinse solvent or solution each time step a) is performed and each time step b) is performed. In an embodiment, a fresh rinse solvent or solution is employed for each rinsing step. In a further embodiment, the same rinse solution is re-used for each rinsing step.

Preferably, steps a) and b) are repeated one or more times until the multilayer film reaches the desired thickness or desired number of layers before the substrate is exposed to the oil, where each cycle deposits a new bilayer on the substrate. In specific embodiments, the multilayer polymer film comprises more than one bilayer. In a further embodiment, steps a) and b) are repeated 2 or more times, 5 or more times, 10 or more times, 20 or more times, 30 or more times, 50 or more times, or 100 or more times. The substrate can be exposed to the solutions containing the polymer solutions using methods known in the art, including but not limited to, dip coating.

The substrate can be any material able to support the formation of the nanoporous or microporous multilayer film, including but not limited to glass, metals and plastics. The substrate can include curved and irregularly shaped three dimensional surfaces, as well as completely solid surfaces and mesh surfaces (e.g., having a porosity between 100 μm and 250 μm). For example, the substrate can be the interior of a tube or container for a liquid or gel where it is undesirable for the contents of the tube or container to stick or adhere to the surface. The first polymer layer, second polymer layer, and oil are therefore selected so that the liquid or gel has reduced adhesion to the container. Alternatively, the substrate can be a display of a sensor where the degree or extent to which a liquid adheres to the substrate indicates the presence of a substance in the liquid.

A further embodiment of the invention provides for patterning the substrate so that the nanoporous or microporous multilayer film is formed on a first specified portion of the substrate. A portion of the multilayer film on the first specified portion of the substrate is further functionalized with an amine, hydroxyl group, thiol group, or hydrazine group having the formula R—NH$_2$, R—OH, R—SH or R—NHNH$_2$, where R is hydrophobic. In a further embodiment, a second specified portion of the substrate is not covered by the oil infused multilayer film, or, alternatively, a portion of the one or more bilayers on the second specified portion of the substrate is further functionalized with an amine, hydroxyl group, thiol group, or hydrazine group having the formula R—NH$_2$, R—OH, R—SH or R—NHNH$_2$, where R is hydrophilic.

Additionally, in a further embodiment, a portion of the one or more bilayers on the first specified portion of the substrate is further functionalized with an amine, hydroxyl group, thiol group, or hydrazine group having the formula R—NH$_2$, R—OH, R—SH or R—NHNH$_2$, where R is hydrophobic, a second specified portion of the substrate is not covered by the oil infused multilayer film, and a third portion of the substrate is covered by a bilayer where a portion of the one or more bilayers on the third specified portion of the substrate is further functionalized with an amine, hydroxyl group, thiol group, or hydrazine group having the formula R—NH$_2$, R—OH, R—SH or R—NHNH$_2$, where R is hydrophilic.

Relative to past approaches to the design of SLIPS using conventional assembly methods, (Sunny et al., Adv. Funct. Mater., 2014, 24: 6658; and Huang et al, ACS Macro Lett., 2013, 2:826) the chemical reactivity of the multilayers used herein is unique, and provides means to chemically tune interactions between the matrix and the infused oil phases. The present invention demonstrates that the spatial control over matrix functionalization can be used to create oil-infused SLIPS with chemically-patterned "sticky" regions devoid of oil ("STICKS") that can prevent or arrest the sliding of aqueous fluids, extract samples of liquid from contacting media, and provide in-plane directional control over the trajectories of sliding droplets.

The first and second polymer layers of the bilayer can comprise any polymers or combination of polymers able to form a stable bilayer and where the first polymer layer is optionally able to be functionalized and the second polymer layer is optionally also able to be functionalized (as described in U.S. Pat. No. 8,071,210). The chemical reactivity of the functionalized bilayers provides means to tune interactions between the matrix and infused oil phases. Spatial control over the functionalization can be used to create SLIPS with regions devoid of oil that can prevent or arrest the sliding of aqueous fluids, extract samples of liquid from contacting media, or provide control over the trajectories of sliding droplets. Preferably, the first polymer layer is covalently cross-linked with the second polymer layer. In further embodiments, the bilayers are reacted with small chemical groups containing a hydrophobic or hydrophilic amine to further functionalize the bilayer (i.e., to install secondary surface functionality).

In an embodiment, the first polymer layer of the bilayer comprises a functionalized azlactone having the formula:

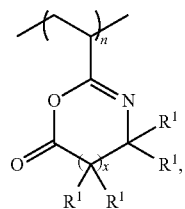

wherein x is 0 or the integers 1 or 2; and each R$^1$ is independently selected from the group consisting of: hydrogen, alkyl groups, alkenyl groups, alkynyl groups, carbocyclic groups, heterocyclic groups, aryl groups, heteroaryl groups, alkoxy groups, aldehyde groups, ether groups, and ester groups, any of which may be substituted or unsubstituted. In an embodiment, the first polymer layer comprises functionalized poly(vinyl-4,4-dimethylazlactone) (PVDMA). In an embodiment, the first polymer layer consists of functionalized poly(vinyl-4,4-dimethylazlactone) (PVDMA). In a further embodiment, the PVDMA was synthesized by free-radical polymerization of PVDMA with intentionally added cyclic azlactone-functionalized oligomer in an amount ranging from 1 wt % to 10 wt %, preferably between 5 wt % and 8 wt %.

Useful functionalized azlactone polymers include, but are not limited to, poly(vinyl-4,4-dimethylazlactone), poly(2-vinyl-4,4-dimethyl-2-oxazolin-5-one), poly(2-isopropenyl-4,4-dimethyl-2-oxazolin-5-one), poly(2-vinyl-4,4-diethyl-2-oxazolin-5-one), poly(2-vinyl-4-ethyl-4-methyl-2-oxazolin-5-one), poly(2-vinyl-4-dodecyl-4-methyl -2-oxazolin-5-one), poly(2-vinyl-4,4-pentamethylene-2-oxazolin-5-one), poly (2-vinyl 1-4-methy 1-4-pheny1-2-oxazolin-5-one), poly(2-isopropenyl-4-benzyl-4-methyl-2-oxazolin-5-one), or poly(2-vinyl-4,4-dimethyl-1,3-oxazin-6-one). Useful azlactone functionalized polymers further include azlactone functionalized polyisoprenes and azlactone functionalized polybutadienes.

In an embodiment, the second polymer layer of the bilayer is optionally functionalized and comprises an amine functionalized polymer, an alcohol functionalized polymer, or a thiol functionalized polymer. Creating specific functionalities with amine, alcohol, and thiol groups is a process well known in the art (for example, see *Bioconjugate Techniques, 2$^{nd}$ Edition*, 2008, Greg T. Hermanson). In embodiments, the second polymer layer comprises an optionally functionalized polymer selected from the group consisting of poly (ethylene imine) (PEI), polylysine, pollyallylamine, poly (amidoamine) dendrimers, polyvinyl alcohol, poly hydroxyl ethyl methacrylate, poly(methacrylic acid) functionalized with cysteamine, and linear and hyperbranched and dendritic polymers functionalized with primary amines, hydroxyl groups, or thiol groups.

In embodiments, the second polymer layer comprises a polymer, which is optionally functionalized, selected from the group consisting of polyolefins, poly(alkyls), poly(alkenyls), poly(ethers), poly(esters), poly(imides), polyamides, poly(aryls), poly(heterocycles), poly(ethylene imines), poly (urethanes), poly(α,β-unsaturated carboxylic acids), poly(α,β-unsaturated carboxylic acid derivatives), poly(vinyl esters of carboxylic acids), poly(vinyl halides), poly(vinyl alkyl ethers), poly(N-vinyl compounds), poly(vinyl ketones), poly (vinyl aldehydes) and any combination thereof. In an embodiment, the second polymer layer comprises poly (ethylene imine) (PEI).

"Functionalized polymer" refers to a polymer in which at least a portion of the individual monomer units are substituted with a specific functional group. For the functionalized polymers of the present invention, at least 1% or more, at least 2% or more, at least 5% or more, at least 10% or more, at least 15% or more, at least 20% or more, at least 30% or more, at least 50% or more, at least 75% or more, or at least 90% or more of the portion of the monomer units is substituted with a specific functional group.

For some embodiments, it may be desirable to further functionalize a portion of the one or more bilayers. This can be achieved, for example, by reacting a portion of any residual functional groups in the one or more bilayers with an amine group, hydroxyl group, thiol group or hydrazine, or by reacting a portion of the first or second polymer with an amine reactive group or hydroxyl reactive group.

In an embodiment, at least a portion of the residual functional groups in the bilayer is reacted such as generally described in Scheme 1 below with an amine, hydroxyl group, thiol group, or hydrazine group having the formula R—NH$_2$, R—OH, R—SH or R—NHNH$_2$, where R is hydrophobic or hydrophilic (it should be noted that the residual functional groups are not limited to azlactone groups)

consisting of methanol, ethanol, propanol, butanol, pentanol, hexanol, heptanol, octanol, nonanol, decanol, and combinations thereof. In further embodiments, at least a portion of the residual functional groups in the bilayer is reacted with a thiol selected from the group consisting of methanethiol, ethanethiol, propanethiol, butanethiol, pentanethiol, hexanethiol, heptanethiol, octanethiol, nonanethiol, decanethiol, and combinations thereof. In an embodiment, at least a portion of the residual functional groups in the bilayer is reacted with an amino sugar, amino alcohol, amino polyol, glucamine (preferably D-glucamine), dimethylaminopropylamine (DMAPA), or combinations thereof. In other embodiments, at least a portion of the residual functional groups in the bilayer is reacted with a hydrazine group to form an acylhydrazine group.

In a further embodiment, at least a portion of the residual functional groups in the bilayer is reacted to form multilayer films with chemically labile amide/ester-, amide/thioester-, and amide/imine-type bonds. These chemically labile bonds are able to be broken, such as through hydrolysis, in order to undergo stimuli-responsive and reversible changes in wetting behaviors. For example, a functionalized layer (not hydrolyzed) can be designed to be hydrophobic while the functionalized layer which has been hydrolyzed to break Scheme 1

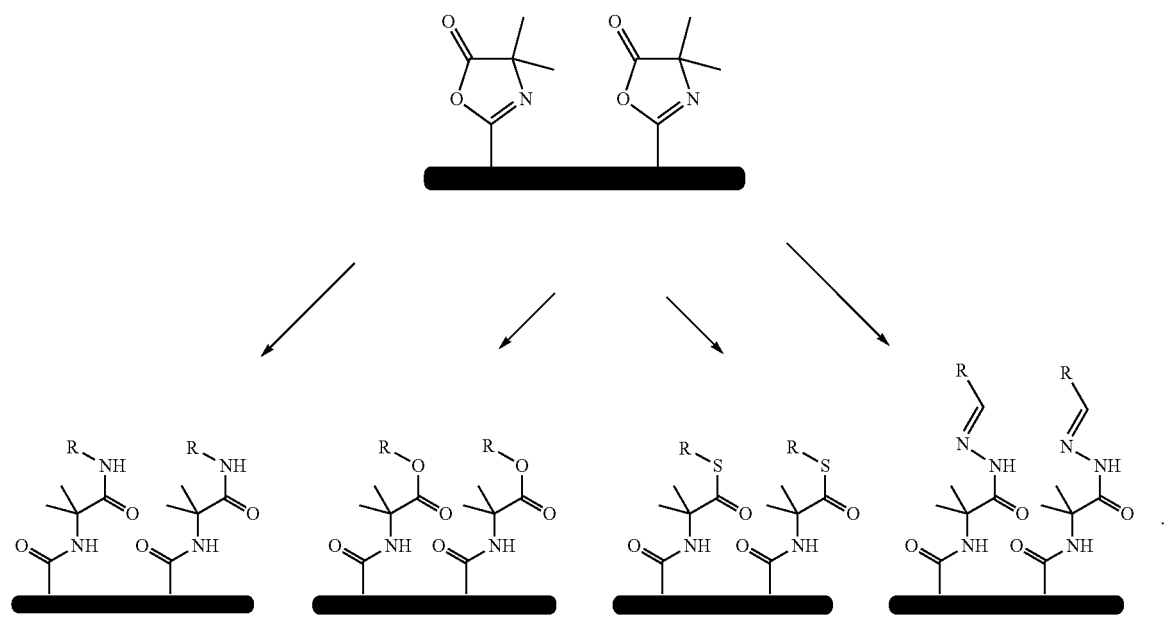

In embodiments, R is a substituted or unsubstituted C$_1$ to C$_{20}$ alkyl group, preferably a C$_1$ to C$_{12}$ alkyl group. In other embodiments, R is a substituted or unsubstituted C$_2$ to C$_{20}$ alkenyl group, preferably a C$_2$ to C$_{12}$ alkenyl group. In further embodiments, at least a portion of the residual functional groups in the bilayer is reacted with an amine selected from the group consisting of methylamine, ethylamine, propylamine, butylamine, pentylamine, hexylamine, heptylamine, octylamine, nonylamine, decylamine, and combinations thereof, preferably n-propylamine, n-octylamine, or n-decylamine. In other embodiments, R is an alkyl group substituted with one or more hydroxyl groups or charged groups such as COO$^-$ or NR3$^+$. In further embodiments, at least a portion of the residual functional groups in the bilayer is reacted with an alcohol selected from the group amide/ester- or amide/thioester-type bonds can be designed to be relatively hydrophilic. In a further embodiment, the invention provides for patterning the substrate so that a nanoporous or microporous multilayer film having a non-hydrolyzed functionalized azlactone layer is formed on a first specified portion of the substrate while the nanoporous or microporous multilayer film having a hydrolyzed functionalized azlactone layer is formed on a second specified portion of the substrate. Preferably, the oil is added to the multilayer film following the hydrolyzing step.

In an embodiment, the polymer of the first polymer layer is further functionalized with a hydrophobic (decylamine or propylamine) or hydrophilic (glucamine) primary amine-containing small molecule.

As used herein, "an oil" refers to a non-polar, hydrophobic chemical substance which is a liquid at ambient temperature and which has no or very low solubility in water. Preferably, the oil infused into the one or more bilayers is selected from the group consisting of a silicone oil, a vegetable oil, a mineral oil, a thermotropic liquid crystal, and combinations thereof. Suitable vegetable oils include, but are not limited to, canola oil, coconut oil, olive oil, soybean oil and combinations thereof.

In an embodiment, a slippery liquid-infused porous surface (SLIPS) coating is provided comprising: a) a multilayer polymer film comprising one or more bilayers where said multilayer polymer film has a nanoscale or microscale porosity, wherein each bilayer comprises a first polymer layer covalently linked with a second polymer layer; and b) an oil selected from the group consisting of a silicone oil, a vegetable oil, a mineral oil, a thermotropic liquid crystal, and combinations thereof, wherein said oil coats at least a portion of the multilayer polymer film and said oil at least partially fills the pores of at least a portion of said multilayer polymer film. Preferably, the multilayer polymer film of the coating has a thickness of 5 µm or less, and comprises one or more PVDMA/PEI bilayers, which are further functionalized with a hydrophobic amine.

A specific embodiment of the present invention provides a SLIPS design based on the infusion of oils into nanoporous or microporous (preferably nanoporous) polymer coatings fabricated by reactive layer-by-layer assembly of polymer multilayers using branched poly(ethylene imine) (PEI) and the amine-reactive polymer poly(vinyl-4,4-dimethylazlactone) (PVDMA). In an embodiment, the multilayer film comprises one or more PVDMA/PEI bilayers, which are further functionalized with a decyl group by reacting with n-decylamine and wherein the one or more bilayers are infused with a silicone oil or an anisotropic thermotropic liquid crystal.

One aspect of the invention provides thin multilayer polymer films and coatings (e.g., equal to or less than 100 µm, equal to or less than 50 µm, preferably less than or equal to 10 µm, preferably less than or equal to 5 µm). Preferably, the multilayer film comprises 2 or more bilayers, 5 or more bilayers, 10 or more bilayers, 20 or more bilayers, 30 or more bilayers, 50 or more bilayers, or 100 or more bilayers. Preferably each first polymer layer alternates with the second polymer layer. In embodiments, the multilayer films have a nanoscale or microscale porosity. Preferably, the multilayer films have a nanoscale porosity.

In an embodiment, SLIPS are infused with a thermotropic liquid crystal (an anisotropic oil) to generate sliding angles and velocities that depend critically upon the chemical compositions of contacting aqueous phases, revealing a novel 'sliding' basis for the sensing and naked-eye detection of environmental analytes, including bacterial endotoxin (i.e., LPS) in aqueous media via visually apparent changes in droplet sliding speeds as a function of analyte concentration. Such LC-infused SLIPS provide opportunities to design slippery surfaces that could permit active and external control over droplet adhesion and mobility.

In an embodiment, the present invention provides a method for detecting an analyte, substance, or impurity in a liquid comprising the steps of:
a) providing a sensor having a first surface area comprising:
  i) a multilayer polymer film comprising one or more bilayers, wherein each bilayer comprises a first polymer layer in contact with a second polymer layer and said multilayer polymer film has a nanoscale or microscale porosity; and
  ii) an oil selected from the group consisting of a silicone oil, a vegetable oil, a mineral oil, a thermotropic liquid crystal, and combinations thereof, wherein said oil coats at least a portion of the multilayer polymer film and said oil at least partially fills the pores of at least a portion of said multilayer polymer film;
wherein said oil infused multilayer polymer film exhibits a hydrophobic or hydrophilic effect on said liquid;
b) providing said liquid to said first surface area;
c) comparing the adhesion of said liquid to said first surface area to a control sample or known standard of said liquid, wherein a change in the adhesion of said liquid to said first surface area indicates an analyte, substance, or impurity in said liquid.

Preferably, the first surface area comprises one or more optionally functionalized PVDMA/PEI bilayers and the oil is a silicone oil. In a further embodiment, the step of comparing the adhesion of the liquid to the first surface area comprises comparing the time the liquid travels across the first surface area. The comparisons can be measured and quantified or even performed using the naked eye. Optionally, the liquid can be dyed or reacted with a compound containing a dye or fluorophore to improve visibility.

In addition, the present invention provides SLIPS which are anti-fouling to bacteria, fungi, and mammalian cells, and that the liquid phases used to impart anti-fouling properties can also be used as reservoirs for the controlled release of other active agents (e.g., antibiotics or anti-biofilm agents, etc.) that can impart additional functions to these slippery surfaces.

Thus, the methods described herein can be used to fabricate physically and chemically durable SLIPS coatings on objects of arbitrary shape, size, and topology (e.g., on curved surfaces, insides of hollow tubes, etc.). Specifically these slippery surfaces could be used as antifouling surfaces, anti-bacterial/fungal surfaces, detectors, and in packaging (e.g., ketchup bottles).

DETAILED DESCRIPTION OF THE INVENTION

Definitions

Figure 1:
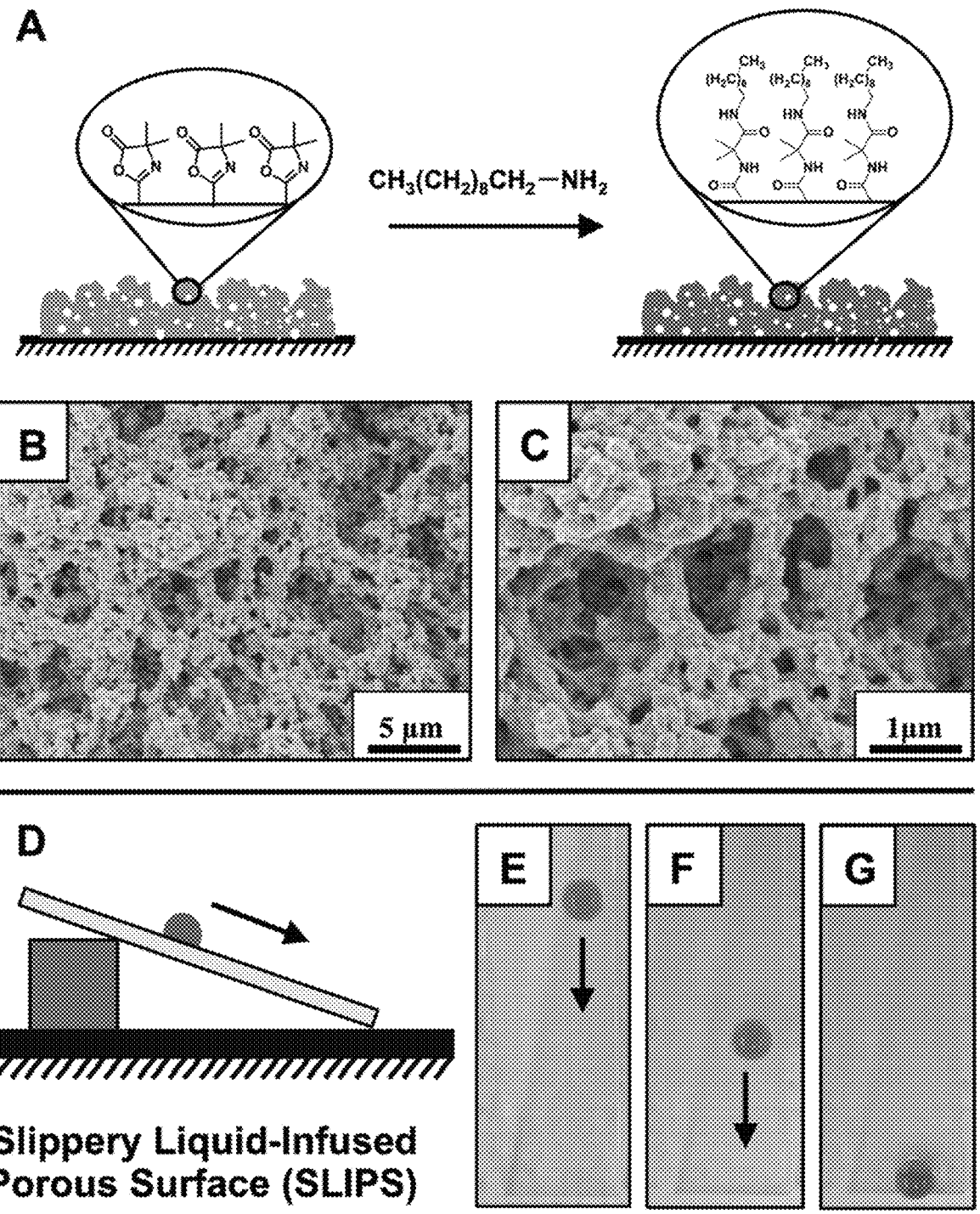
FIG. 1. A) Schematic showing post-fabrication functionalization of residual azlactone groups in nanoporous PEI/PVDMA multilayers by reaction with n-decylamine in one embodiment of the invention. B and C) Low- and high-magnification SEM images of multilayers in one embodiment showing micro- and nanoscale porosity. D) Schematic showing droplet of water sliding on a tilted oil-infused porous surface. E-G) Top-down images showing a droplet of aqueous TMR (10 µL; tilt angle≈10°) sliding on a silicone oil-infused multilayer.

An "amine reactive group" or "hydroxyl; reactive group" can be any functional group able to react with an amine group or hydroxyl group, respectively.

As used herein, the term "anti-fouling" refers to a material's ability to resist adhesion by an undesirable material, such as oils, organic compounds, and organisms. In particular, it is desirable to prevent or reduce the adhesion of hydrophobic compounds and organisms to a material which is submerged or in contact with water.

The term "nanoscale" refers to a length less than 1,000 nm, preferably less than 100 nm, and the term "microscale" refers to a length less than 1,000 μm, preferably less than 100 μm.

The term "alkyl" refers to a monoradical of a branched or unbranched (straight-chain or linear) saturated hydrocarbon and to cycloalkyl groups having one or more rings. Alkyl groups as used herein include those having from 1 to 20 carbon atoms, preferably having from 1 to 12 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cycloalkyl groups include those having one or more rings. Cyclic alkyl groups include those having a 3-, 4-, 5-, 6-, 7-, 8-, 9-, 10-, 11- or 12-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups.

The term "alkenyl" refers to a monoradical of a branched or unbranched unsaturated hydrocarbon group having one or more double bonds and to cycloalkenyl groups having one or more rings wherein at least one ring contains a double bond. Alkenyl groups include those having 1, 2 or more double bonds and those in which two or more of the double bonds are conjugated double bonds. Alkenyl groups include those having from 2 to 20 carbon atoms, preferably having from 2 to 12 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9-, 10-, 11- or 12-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

The term "aryl" refers to a chemical group having one or more 5-, 6- or 7-member aromatic or heterocyclic aromatic rings. An aromatic hydrocarbon is a hydrocarbon with a conjugated cyclic molecular structure. Aryl groups include those having from 4 to 30 carbon atoms, preferably having from 6 to 18 carbon atoms. Aryl groups can contain a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Heterocyclic aromatic rings can include one or more N, O, or S atoms in the ring. Heterocyclic aromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following benzene, naphthalene, naphthoquinone, diphenylmethane, fluorene, fluoranthene, anthracene, anthraquinone, phenanthrene, tetracene, naphthacenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed above provided in a covalently bonded configuration in the compounds of the present invention. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl and alkenyl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl groups and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R is H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

As used herein, the term "alkylene" refers to a divalent radical derived from an alkyl group or as defined herein. Alkylene groups in some embodiments function as attaching and/or spacer groups in the present compositions. Compounds of the present invention include substituted and unsubstituted $C_1$-$C_{30}$ alkylene, $C_1$-$C_{12}$ alkylene and $C_1$-$C_5$ alkylene groups. The term "alkylene" includes cycloalkylene and non-cyclic alkylene groups.

As used herein, the term "cycloalkylene" refers to a divalent radical derived from a cycloalkyl group as defined herein. Cycloalkylene groups in some embodiments function as attaching and/or spacer groups in the present compositions. Compounds of the present invention include substituted and unsubstituted $C_1$-$C_{30}$ cycloalkenylene, $C_1$-$C_{12}$ cycloalkenylene and $C_1$-$C_5$ cycloalkenylene groups.

As used herein, the term "alkenylene" refers to a divalent radical derived from an alkenyl group as defined herein. Alkenylene groups in some embodiments function as attaching and/or spacer groups in the present compositions. Compounds of the present invention include substituted and unsubstituted $C_1$-$C_{20}$ alkenylene, $C_1$-$C_{12}$ alkenylene and $C_1$-$C_5$ alkenylene groups. The term "alkenylene" includes cycloalkenylene and non-cyclic alkenylene groups.

As used herein, the term "cycloalkenylene" refers to a divalent radical derived from a cylcoalkenyl group as defined herein. Cycloalkenylene groups in some embodiments function as attaching and/or spacer groups in the present compositions.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As used herein, the term "halo" refers to a halogen group such as a fluoro (—F), chloro (—Cl), bromo (—Br) or iodo (—I).

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Fabrication of SLIPS Materials

A number of nanoporous PEI/PVDMA coatings (~3.5 micrometers thick) were fabricated and then functionalized by reaction with n-decylamine to impart hydrophobic character. Silicon oil was infused for the model oil phase. The infused nanoporous films were subjected to a number of tests to demonstrate their capabilities and their ability to retain their desired characteristics (e.g., repeated bending and flexing, creasing, stretching, deep scratching, and surface abrasion). SLIPS fabricated by infusion of silicone oil were stable and slippery when contacted with a broad range of chemically complex liquids (e.g., acidic and alkaline solutions, unfiltered eutrophic lake water, serum-containing cell culture medium, seawater, and ketchup). Additional oils were also infused for comparison including canola, coconut, and olive oil.

One aspect of the invention provides an infusion of a thermotropic liquid crystal (an anisotropic oil) yielding SLIPS with sliding angles and velocities that depend critically upon the chemical compositions of contacting aqueous phases, revealing a novel "sliding" basis for the sensing and naked-eye detection of environmental analytes, including bacterial endotoxin, in aqueous media.

It is anticipated that these approaches will also be useful for the design of advanced and multifunctional anti-fouling surfaces that provide control over the avoidance, manipulation, transport, collection, and detection of aqueous fluids in fundamental and applied contexts. These results provide new principles and expand the range of tools that can be used to manipulate the properties and behaviors of liquid-infused anti-fouling surfaces and open the door to new potential applications of this emerging class of slippery soft materials.

It is to be understood that this invention is not limited to only the specific methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

Example 1

In an embodiment, azlactone-functionalized multilayers are fabricated using poly(vinyl-4,4-dimethylazlactone) (PVDMA) and branched poly(ethyleneimine) (PEI) to explore the feasibility of this approach, for several reasons: i) PEI/PVDMA multilayers are covalently cross-linked and, thus, chemically robust and physically durable, ii) residual azlactone functionality in these coatings can be used to tune surface and bulk wetting behaviors by treatment with strategically-selected amine functionalized molecules (e.g., FIG. 1 (A)), and iii) they can be fabricated with micro- and nanoporous morphologies containing voids and other features (FIGS. 1 (B) and (C)) that can trap and host secondary liquid phases (Buck et al., Adv. Mater. (2007), 19:3951; Manna et al., Adv. Funct. Mater. (2015), 25:1672; Manna et al., Adv. Mater. (2013), 25:5104; Manna et al., Adv. Mater. (2012), 24:4291; and Buck et al., Chem. Mater. (2010), 22:6319).

For the studies described here, nanoporous PEI/PVDMA coatings≈3.5±0.9 μm-thick were used and functionalized by reaction with n-decylamine (FIG. 1 (A)) to impart hydrophobic character; and silicon oil was used as a model oil phase. Infusion of oil into porous multilayers fabricated on planar glass yielded stable oil-infused SLIPS that allowed droplets of aqueous solutions to slide off unimpeded (see FIG. 1 (D)). FIG. 1 (E)-(G) shows top-down views of an aqueous droplet of tetramethylrhodamine (TMR) (10 µL) placed at the upper end of a slippery surface tilted at ≈10°; the droplet was observed to slide down the surface at a rate of 2.9 mm s$^{-1}$. Droplets of this size also slid down these surfaces at angles as low as 1° (albeit more slowly, at a rate of 0.133 mm s$^{-1}$).

Example 2

Figure 2:
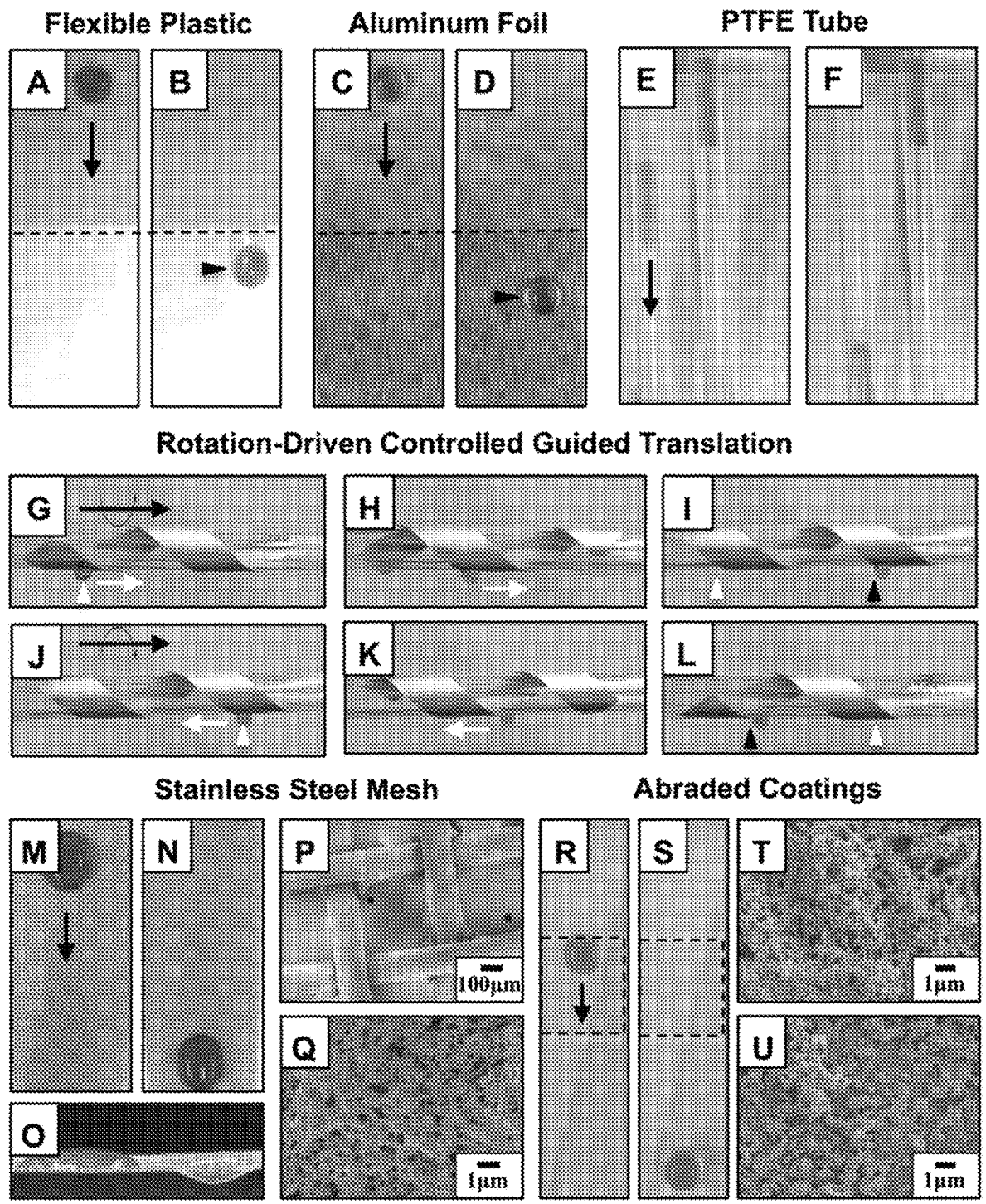
FIG. 2. A-D) Top-down views of droplets of aqueous TMR (10 µL) sliding down silicone oil-infused multilayers fabricated on PET film (A) and (B) and aluminum foil (C) and (D); tilt angle≈10°; dotted lines show borders between SLIPS-coated (top) and uncoated regions (bottom) of each panel. E and F) Sliding of aliquots of aqueous TMR (20 µL; tilt angle≈3°) inside SLIPS-coated flexible PTFE tubing (left side of each panel); the right of each panel shows plugs of aqueous TMR in uncoated tubes. G-L) Images showing a strip of SLIPS-coated aluminum foil wrapped around a bare glass tube. M and N) A droplet of aqueous TMR (50 µL) sliding on SLIPS-coated stainless-steel wire mesh. O) Motor oil (bottom of mesh) can pass through the mesh, but water (top of mesh) cannot, providing principles for oil/water separation. P and Q) SEM images of multilayers on wire mesh prior to oil infusion. R and S) Droplets of aqueous TMR sliding on a SLIPS-coated glass slide after severe abrasion by rubbing with sandpaper; the dotted boxes show the location of the abraded region. T and U) SEM images of non-abraded (T) and sandpaper-abraded (U) multilayers in (R) and (S) after extraction of silicone oil.

This reactive layer-by-layer approach described in Example 1 is well suited for fabrication of SLIPS on surfaces of arbitrary shape and composition. FIG. 2 (A)-(D) shows top-down images of droplets of aqueous TMR sliding on flexible plastic film (A,B) and aluminum foil (C,D) coated with oil-infused PEI/PVDMA multilayers (dotted lines show borders between SLIPS-coated (top) and uncoated (bottom) regions; droplets slid freely at angles of ≈10° on coated regions (A,C), and came to rest upon contact with uncoated regions (B,D)).

Figure 5:
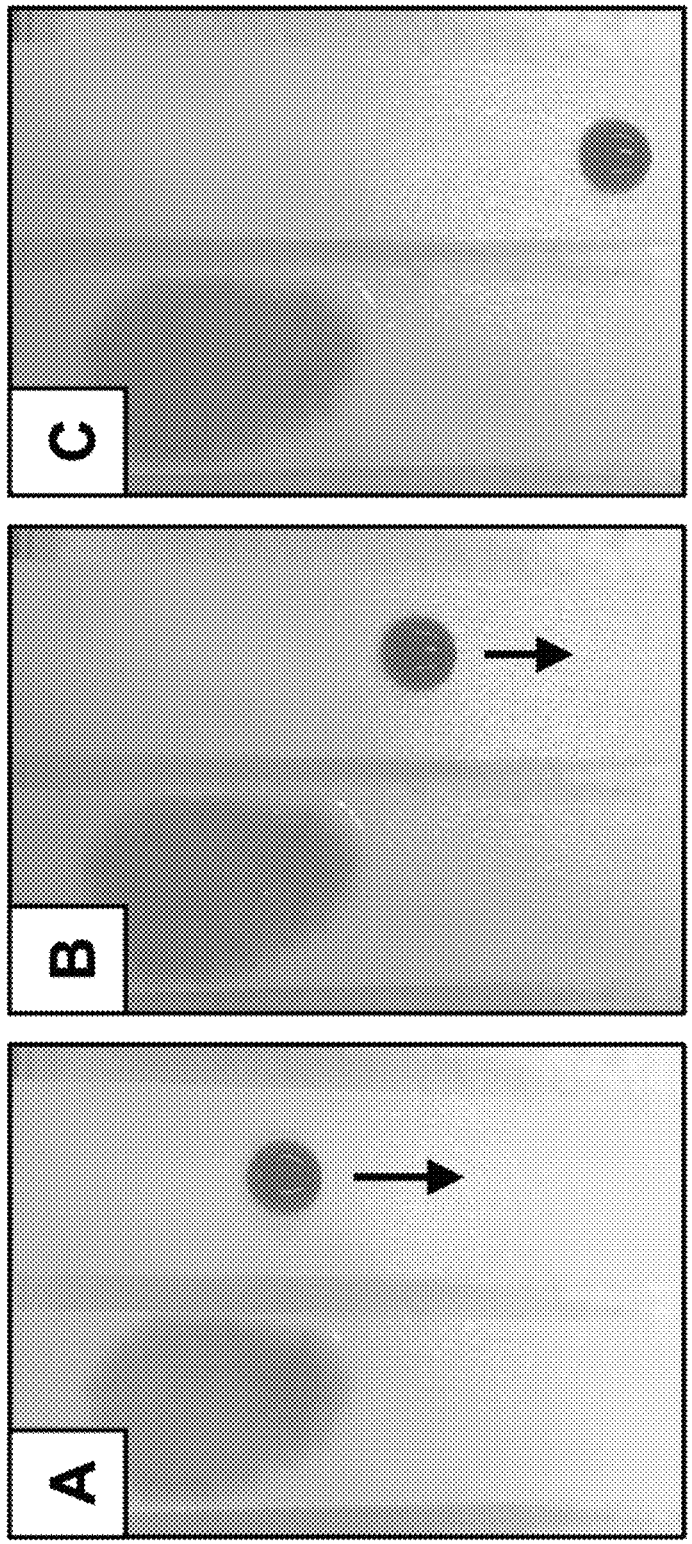
FIG. 5. A-C) Digital photographs showing aqueous droplets of TMR (10 μL) placed on samples of treated filter paper in one embodiment of the invention. The right sample in each panel shows a droplet sliding down the surface of filter paper coated with decylamine-functionalized multilayers infused with silicone oil (tilt angle~10°). The left sample in each panel shows the behavior of a droplet of TMR placed on a control sample of oil-infused filter paper (with no porous multilayer coating; tilt angle~10°).
Figure 6:
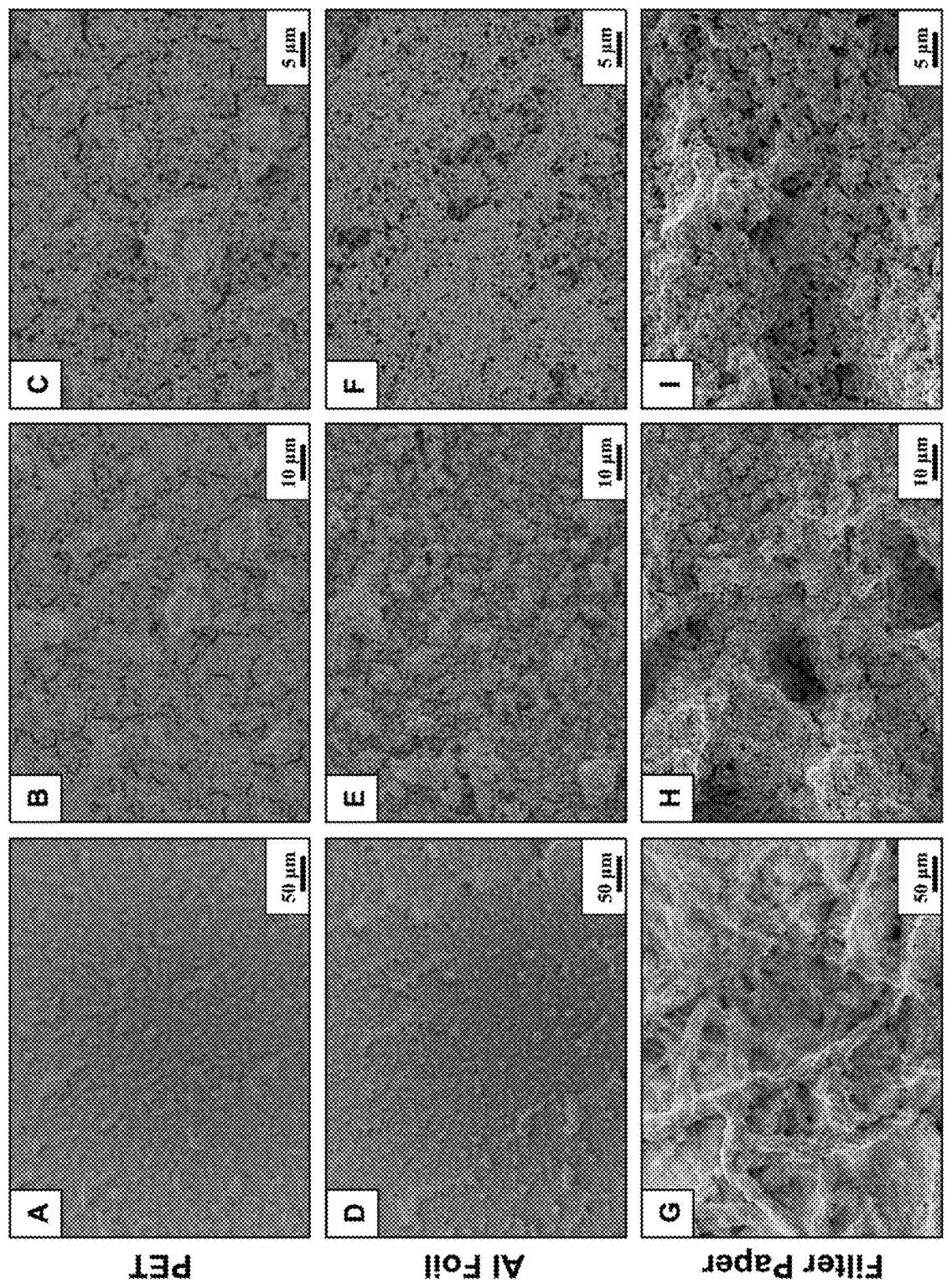
FIG. 6. A-I) SEM images of decylamine-treated PEI/PVDMA multilayers (prior to the infusion of oil) fabricated on the surfaces of (A)-(C) planar PET film, (D)-(F) aluminum foil, and (G)-(I) laboratory filter paper. For each series (A)-(C), (D)-(F), and (G)-(I), samples were imaged at three different magnifications.
Figure 7:
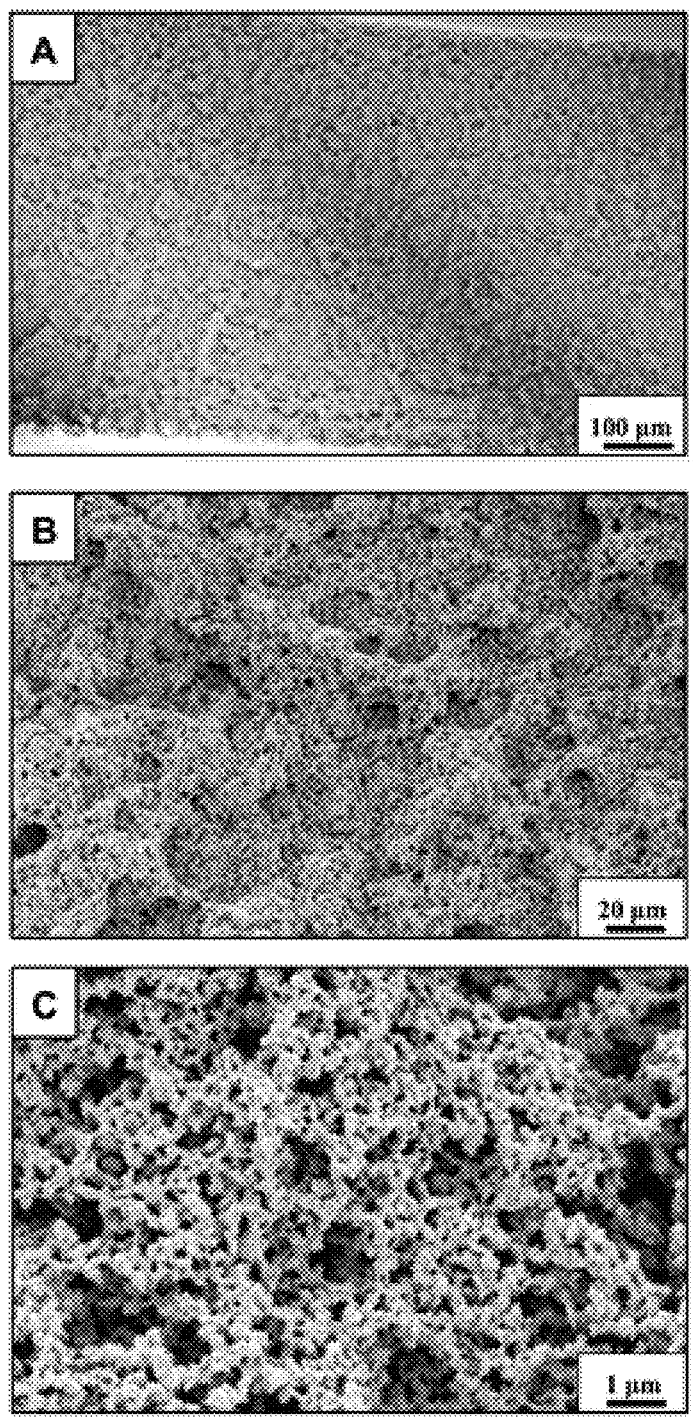
FIG. 7. A-C) SEM images, at three different magnifications, of nanoporous multilayers (prior to the infusion of oil) fabricated on the inner (luminal) surfaces of flexible PTFE tubes (inner dia.=1.15 mm).
Figure 8:
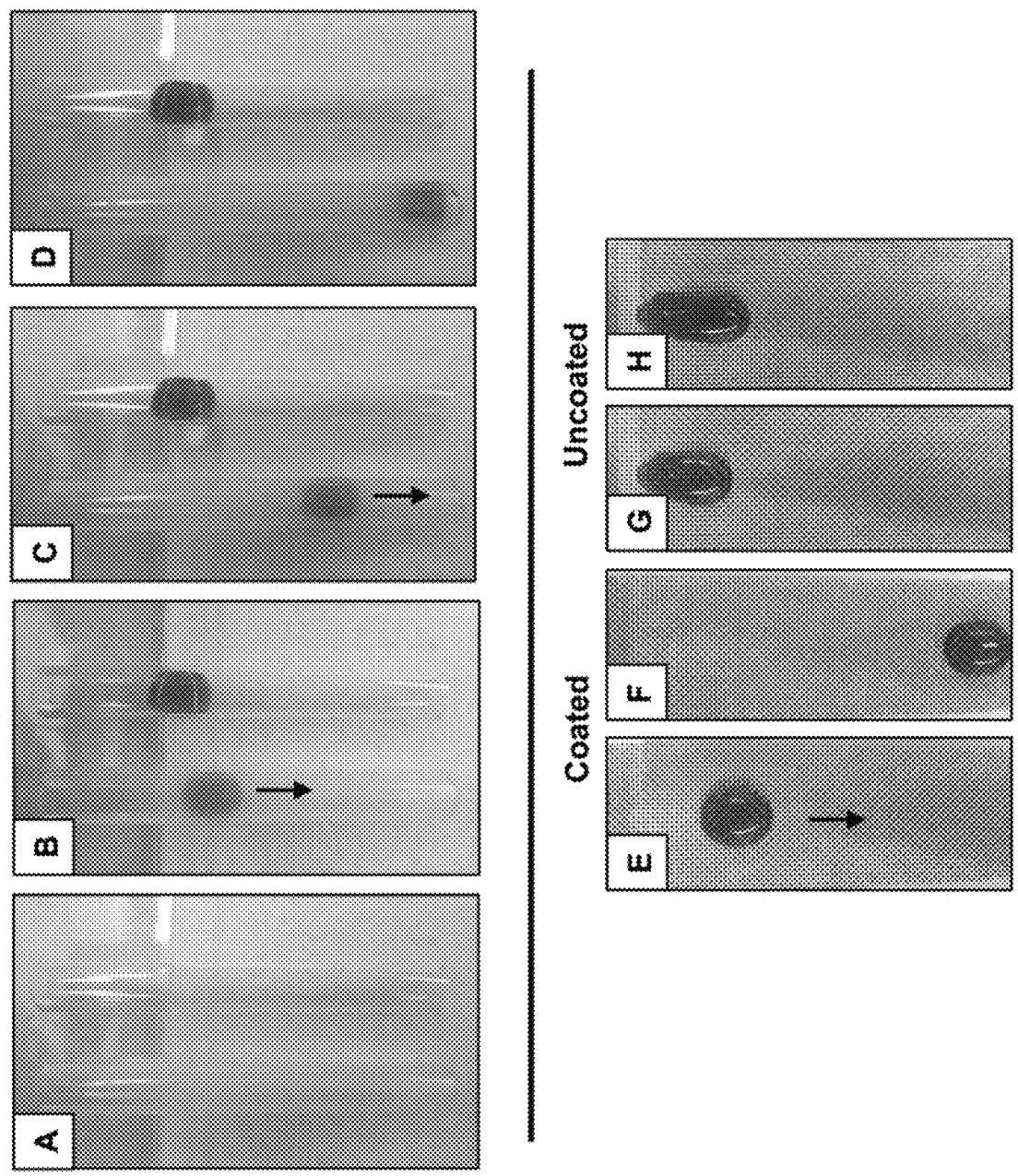
FIG. 8. A-D) Digital photographs showing hollow glass tubes (right side of each panel) and hollow glass tubes with SLIPS-coated inner surfaces (left side of each panel). The images in (B)-(D) show the behaviors of droplets of aqueous TMR (20 μL) placed in the tubes: droplets slid readily in SLIPS-coated samples and remained stuck as plugs in bare, uncoated tubes (tilt angle~3°). E-F) Digital images showing droplets of aqueous TMR (50 μL) sliding down samples of stainless steel wire mesh (wire dia. ~90 μm, pore size=126.3±3.5 μm) coated with oil-infused multilayers (tilt angle~3°). G-H) An experiment identical to that shown in (E)-(F), but performed using samples of bare, uncoated mesh.

FIGS. 5 and 6 show images of droplets sliding on SLIPS-coated filter paper and scanning electron microscopy (SEM) images of the multilayers in FIG. 2 (A)-(D) prior to oil infusion. This approach can also be used to fabricate SLIPS on the inner (luminal) surfaces of tubes. FIG. 7 shows SEM images of multilayers coated on the insides of flexible poly(tetrafluoroethylene) (PTFE) tubing (inner diameter=1.15 mm). FIGS. 2 (E) and (F) (left side of each panel) shows drops of aqueous TMR (20 µL) placed in the tubes after infusion of oil (droplets in uncoated PTFE tubes are shown at the right of each panel). These images reveal plugs of aqueous fluid (θ≈100°) to slip rapidly through the coated tubes at tilt angles as low as 3° (in contrast, fluid in uncoated tubes remained stationary, even at tilt angles of 90°; FIG. 8 shows similar experiments using SLIPS-coated glass tubes. Finally, panels (M) and (N) of FIG. 2 show a droplet of aqueous TMR on stainless-steel wire mesh coated with oil-infused multilayers. Droplets also slipped and slid readily on these topologically complex substrates (at angles as low as 3°; droplets on uncoated mesh shown in FIG. 8. The results suggest these SLIPS to be coated uniformly on the wires comprising the mesh; SEM images prior to oil infusion (FIGS. 2 (P) and (Q)) provide support for this conclusion.

Figure 9:
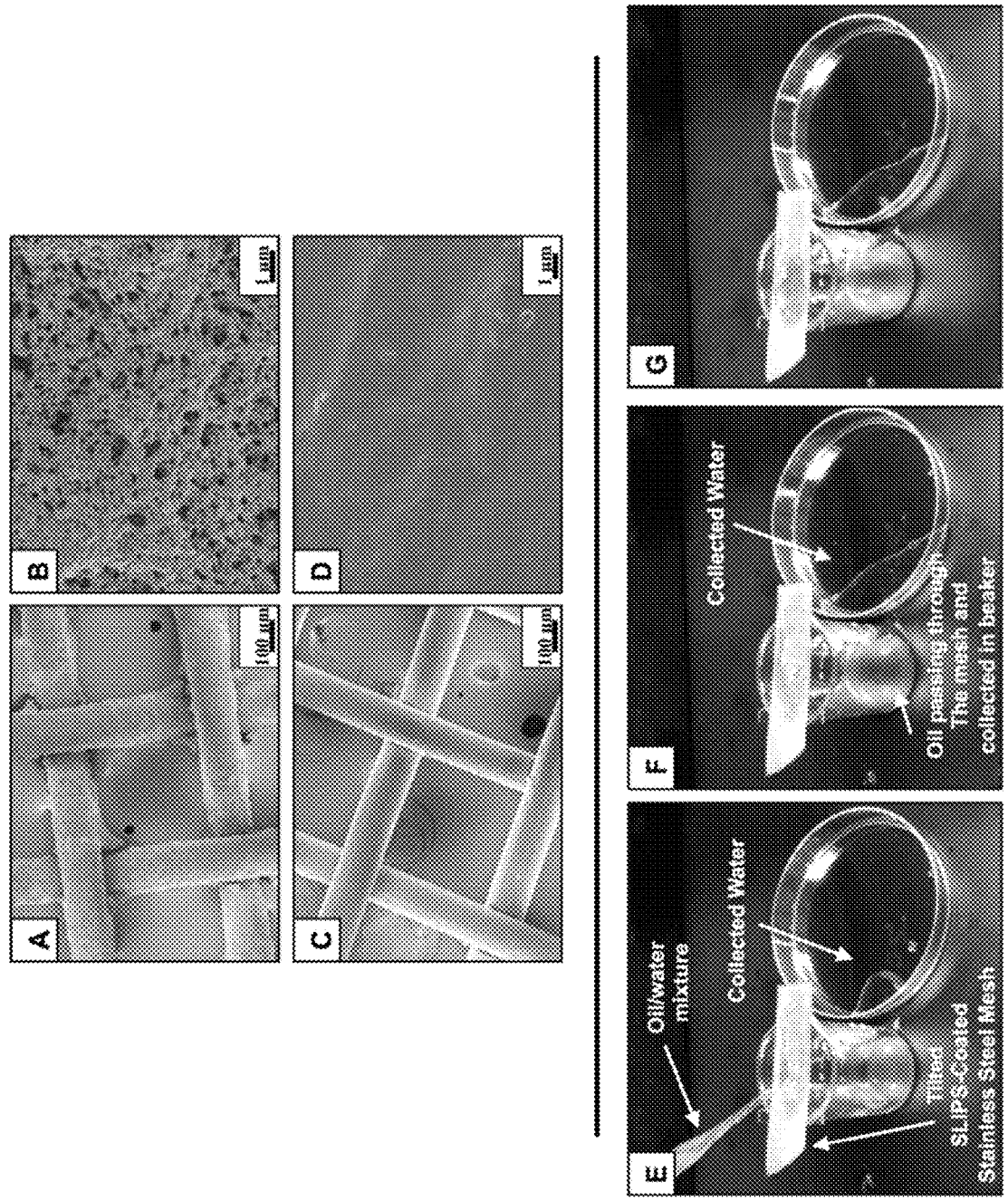
FIG. 9. A-B) Low- and high-magnification SEM images showing the morphology, topography, and porosity of multilayers fabricated on stainless steel wire mesh (wire dia.~90 μm, pore size=126.3±3.5 μm). C-D) SEM images of bare, uncoated stainless steel wire mesh. E-G) Proof-of-concept experiments demonstrating principles for the low-energy, gravity-driven separation of oil/water mixtures using SLIPS-coated surfaces. Stainless steel wire mesh coated with nanoporous decylamine-functionalized polymer multilayers (A)-(B) were infused with a conventional automotive motor oil, placed over the open mouth of a laboratory beaker, and maintained at a tilt angle of ~2° by supporting one side of the mesh using a glass chip (E). A mixture (3:2, v/v) of motor oil and water (or other aqueous solutions) was then poured onto the coated mesh. Oil passed through the mesh and was collected in the beaker below; water did not pass through the mesh, but slid down the slippery surface of the mesh and was collected in a secondary container (F)-(G).

Multilayer-coated mesh infused with motor oil (rather than silicone oil) were also slippery and impermeable to water, but allowed motor oil to pass through unimpeded (FIG. 2 (O)), providing principles useful for the gravity-driven separation of oil/water mixtures using slippery surfaces (see FIG. 9).

Figure 10:
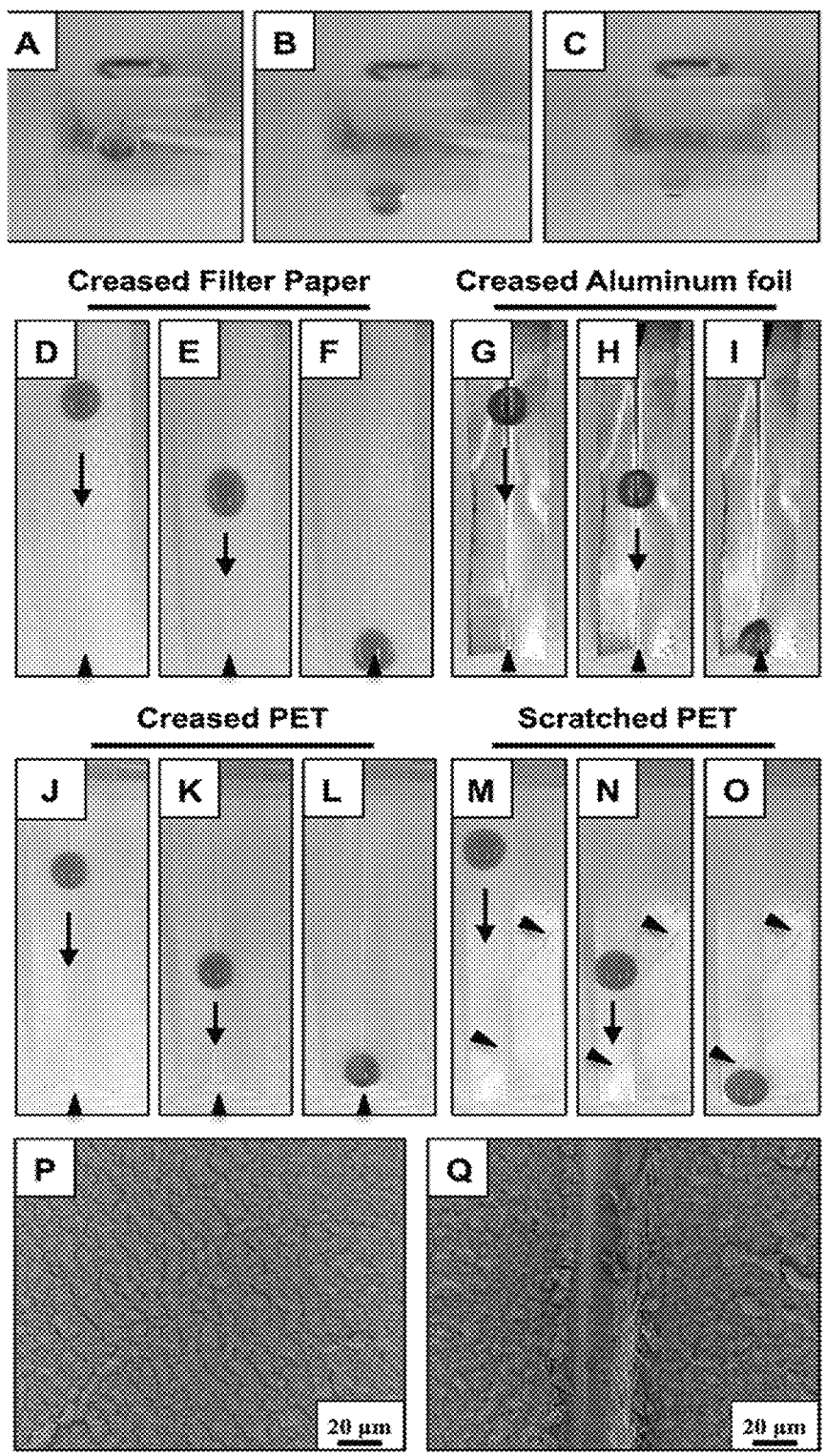
FIG. 10. A-O) Digital photographs demonstrating the retention of slippery properties of substrates coated with oil-infused multilayers after bending, flexing, creasing, and scratching. A-C) Top-down perspective showing a droplet of aqueous TMR (10 μL) sliding on a sample of SLIPS-coated PET plastic film bent and held end-to-end. D-L) Images showing the sliding of aqueous droplets of TMR (10 μL) on SLIPS-coated filter paper (D-F), aluminum foil (G-I), and PET film (J-L); SLIPS coated substrates were permanently creased prior to placing the aqueous droplets, and the aqueous droplets were observed to contact and wet the crease (marked by the locations of the black arrowheads). M-O) Digital images showing the sliding of a droplet of aqueous TMR on a SLIPS-coated PET substrate that was severely scratched in multiple locations (marked by black arrowheads); the droplet was observed to slide unperturbed over the scratches. P-Q) SEM images of a creased multilayer showing the creased region (P) and a scratched polymer film showing the scratched region (Q). Images were acquired after leaching of the infused oil phase.

The physically robust nature of PEI/PVDMA multilayers (Manna et al., Adv. Mater. (2012), 24:4291; and Manna et al., Adv. Mater. (2013), 25:5104) allowed the oil-infused SLIPS described above to maintain slippery properties upon repeated bending and flexing, permanent creasing, and deep scratching (FIG. 10) (Yao et al., Nat. Mater. (2013), 12:529; Wei et al., Adv. Mater. (2014), 26:7358; and Vogel et al., Nat. Commun. (2013), 4:2176). This feature also permitted SLIPS to be cut into arbitrary shapes and transferred to other complex surfaces to endow them with slippery properties (e.g., as demonstrated in FIG. 2 (G)), which shows a strip of SLIPS-coated aluminum foil wrapped on a glass tube; in this proof-of-concept demonstration, transfer of a slippery "track" permits facile rotation-driven control over the transfer of aqueous drops; FIG. 2 (G)-(L)). The images in FIG. 2 (G)-(L) demonstrate how the approach of the present invention can be used to control the lateral transfer of aqueous droplets: a droplet placed at one end can be guided left and right along the slippery track by rotation of the tube clockwise or anti-clockwise.

Figure 11:
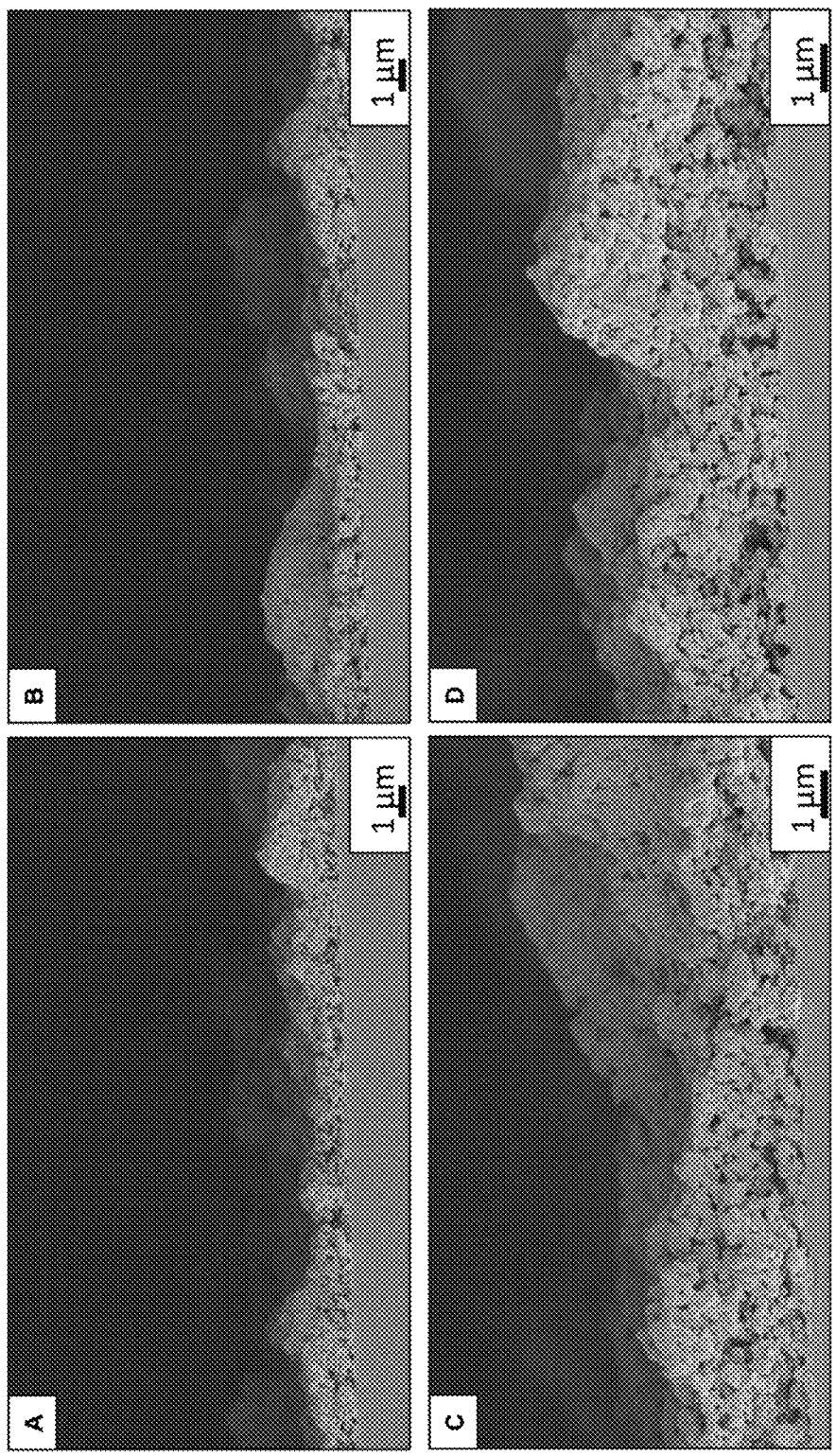
FIG. 11. A-D) Representative SEM images of cross sections of a porous PEI/PVDMA multilayer revealing the porous structure to extend throughout the bulk of the coating at low (A)-(B) and high (C)-(D) magnifications.

Further, because the hydrophobic nature of nanoporous PEI/PVDMA multilayers extends throughout the bulk of the films (FIG. 11), these SLIPS are also able to withstand other forms of severe physical abuse without loss of slippery properties. FIGS. 2 (R) and (S) show a SLIPS-coated surface that was severely abraded by aggressively rubbing the surface with abrasive sand paper (resulting in substantial loss of both oil and porous coating by visual inspection). The dotted boxes in FIGS. 2 (R) and (S) show the location of the abraded region; when combined, these images reveal the coatings to remain slippery despite removal of large amounts of the oil-infused matrix. SEM characterization after leaching of infused oil (FIG. 2 (U)) revealed abrasion to unmask underlying layers of porous material with a morphology similar to that of the original matrix (FIG. 2 (T)) that is sufficient to maintain and host a thin layer of infused oil after severe surface erosion. Finally, the slippery properties of these materials remained unaltered after other physical and chemical insults experienced during repeated freezing and thawing, immersion in boiling water, and exposure to steam-sterilization cycles in an autoclave.

Example 3

Figure 3:
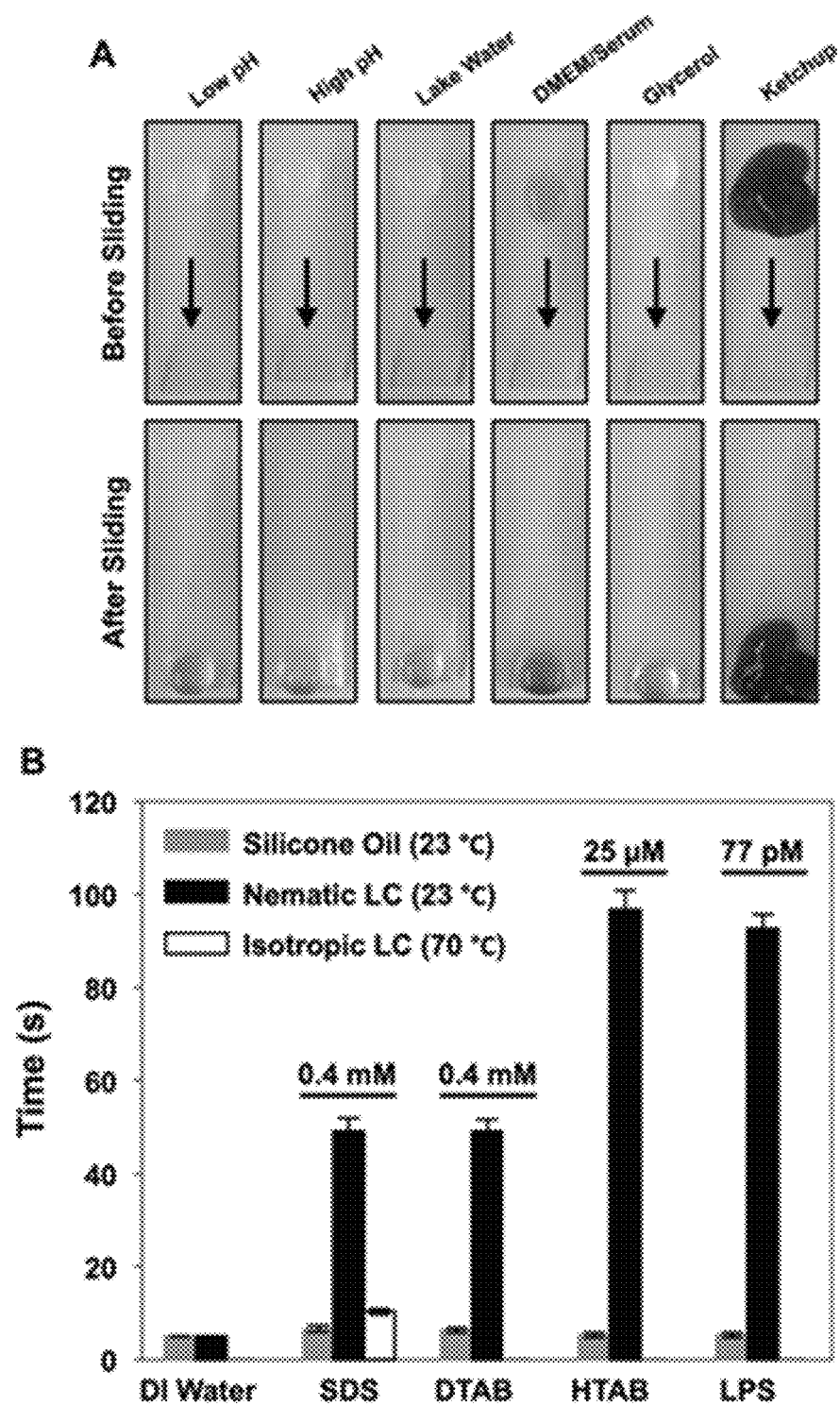
FIG. 3. A) Images showing samples of chemically complex media sliding down a glass slide coated with silicone oil-infused multilayers: acidic and alkaline water, unfiltered eutrophic lake water, serum-containing cell-culture medium, glycerol, and ketchup are shown. B) Plot showing sliding behaviors of droplets of DI water or aqueous droplets containing SDS ($0.4\times10^{-3}$ M), DTAB ($0.4\times10^{-3}$ M), HTAB ($25\times10^{-6}$ M), or LPS ($77\times10^{-12}$ M) on multilayers infused with silicone oil (gray bars) or the thermotropic liquid crystal E7 (black bars) at 23° C.; the white bar shows the sliding behavior of an aqueous droplet of SDS on E7-infused multilayers equilibrated to a temperature of 70° C., well above the nematic/isotropic transition temperature ($\approx$60° C.) for this LC; results are expressed as the time required for a 10 μL droplet to slide 2 cm.
Figure 12:
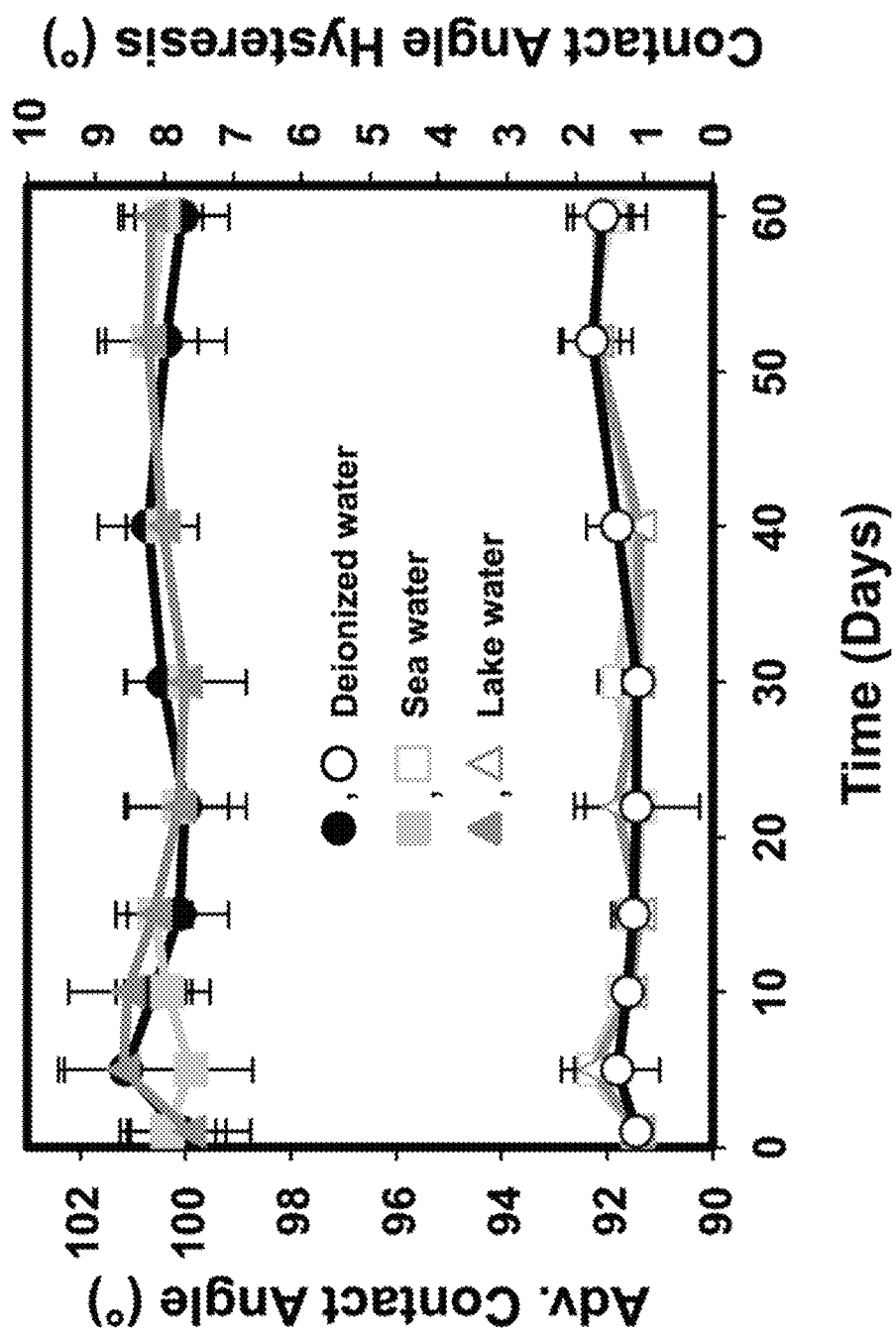
FIG. 12. Plot of advancing water contact angle (closed symbols) and contact angle hysteresis (open symbols) versus time (in days) for multilayers infused with silicone oil immersed for prolonged periods in deionized water (circles), simulated seawater (squares), or unfiltered eutrophic lake water (triangles).

SLIPS fabricated by infusion of silicone oil were stable and slippery when contacted with a broad range of chemically complex liquids (including acidic and alkaline solutions, unfiltered eutrophic lake water, serum-containing cell culture medium, and ketchup; FIG. 3 (A)), and slippery properties were maintained upon incubation in simulated seawater for at least 2 months (FIG. 12). Infusion of other natural and biocompatible oils into these porous coatings yielded surfaces that were slippery to a similar range of liquid media, but afforded additional control over oil adhesiveness and droplet sliding. Table 1 (below) shows contact angle hysteresis and sliding velocities for droplets of water placed on multilayers (tilted at 10°) infused with silicone, canola, coconut, or olive oils. Hysteresis increased monotonically across this series, and sliding velocities decreased substantially with an increase in hysteresis (e.g., from 6 mm s$^{-1}$ for silicone oil to ≈110 µm s$^{-1}$ for droplets on films infused with olive oil). Past studies have demonstrated that the velocities of liquid droplets on SLIPS can be manipulated by changing the viscosity of the infused lubricant (with low viscosity liquids resulting in higher velocities) (Daniel et al., Appl. Phys. Lett. (2013), 102:231601). The viscosities of the oils used here, however, vary over a much smaller range (from 40 to 100 cps) than those used in past studies (from 1 to 2500 cps), and the sliding velocities in Table 1 do not vary monotonically with these small changes.

TABLE 1

Influence of infused oils on SLIPS

| Infused Lubricant | $\theta_{Adv}$ (°) | $\theta_{Hyst}$ (°) | Velocity (mm/s) |
|---|---|---|---|
| Silicone oil | 101.2 ± 1.3 | 2.1 ± 1.1 | 6.0 ± 0 |
| Canola oil | 89.4 ± 1.1 | 5.3 ± 1.5 | 3.4 ± 0.4 |

TABLE 1-continued

Influence of infused oils on SLIPS

| Infused Lubricant | $\theta_{Adv}$ (°) | $\theta_{Hyst}$ (°) | Velocity (mm/s) |
|---|---|---|---|
| Coconut oil | 82.7 ± 0.9 | 10.2 ± 1.5 | 0.23 ± 0.01 |
| Olive oil | 81.3 ± 1.2 | 13.5 ± 2.1 | 0.11 ± 0.01 |

Table 1 shows wetting behaviors (advancing contact angles and contact angle hysteresis) and sliding velocities of droplets of water (20 µL) on multilayers infused with silicone, canola, coconut, and olive oils (tilt angle≈10°).

Figure 13:
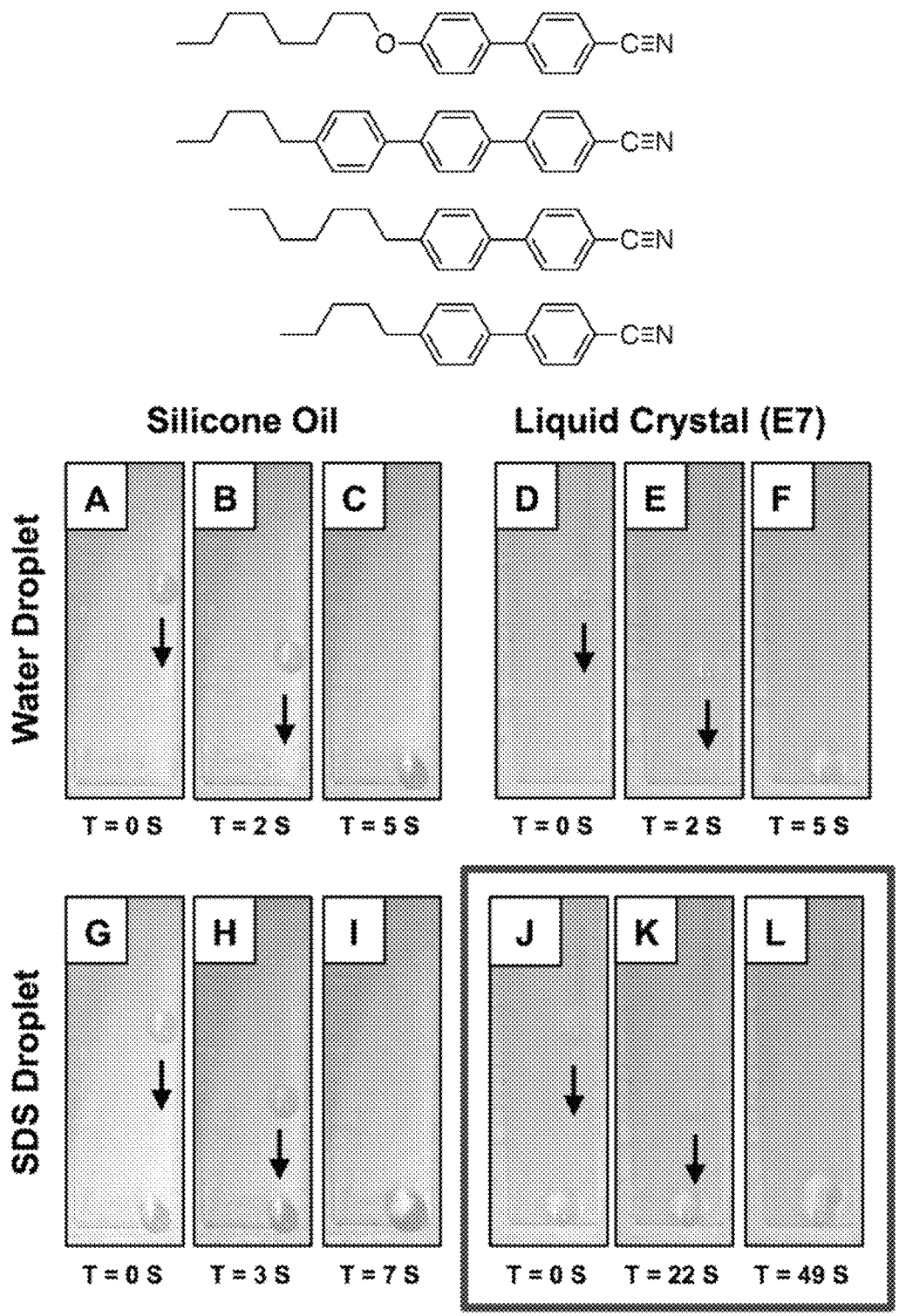
FIG. 13. Top) Structure of the small-molecule thermotropic liquid crystal E7, an anisotropic oil consisting of a mixture of four different cyanobiphenyls containing long aliphatic chains. A-L) Digital photographs showing the sliding behaviors of 10 μL droplets of (A)-(F) deionized water or (G)-(L) an aqueous solution of SDS (0.4 mM) on decylamine functionalized multilayers infused with either silicone oil (A)-(C) and (G)-(I) or E7 (D)-(F) and (J)-(L). All samples were tilted at angles of ~13°. Also shown are the times required for the droplets to slide down the SLIPS-coated surfaces over a distance of 2 cm. Droplets of water traversed this distance in ~5 seconds regardless of the identity of the infused oil (A)-(C) and (D), (F). Droplets of aqueous SDS traversed this distance in ~7 seconds on silicone oil-infused SLIPS (G)-(I), but required ~49 seconds to traverse this distance on E7-infused SLIPS ((J)-(L); box).

The results of additional experiments using multilayers infused with a thermotropic liquid crystal (LC; an anisotropic oil) revealed additional principles useful for control over the mobility of aqueous droplets on SLIPS-coated surfaces. The results in FIG. 3 (B) show the times required for 10 µL droplets of either deionized (DI) water or water containing one of four different amphiphiles [sodium dodecyl sulfate (SDS), dodecyltrimethylammonium bromide (DTAB), hexadecyltrimethylammonium bromide (HTAB), or bacterial endotoxin (lipopolysaccharide, LPS)] to slide 2.0 cm down multilayer-coated surfaces infused with either: i) silicone oil (gray bars) or ii) the small molecule nematic liquid crystal E7 (black bars; at tilt angles of 13°; the structure of E7 is shown in FIG. 13). At ambient temperature (23° C.), droplets of DI water traversed this distance in ≈5 s on both types of slippery surfaces (FIG. 13 shows images of the sliding droplets in these experiments). These results reveal that droplets containing SDS (at $0.4 \times 10^{-3}$ M) require ≈7 s to slide this distance on films infused with silicon oil (gray; similar to results exhibited by DI water). Further inspection, however, reveals droplets containing $0.4 \times 10^{-3}$ M SDS to slide ≈10 times more slowly on E7-infused surfaces (black; over ≈49 s).

It is well known that amphiphiles with long hydrophobic tails can interact with LCs at aqueous/LC interfaces and promote orientational changes in the ordering of the LC (e.g., from planar to homeotropic anchoring) (Brake et al., Science (2003), 302:2094; and Bai et al., Langmuir (2011), 27:5719). It is speculated that differences in the sliding velocities of SDS-containing droplets on E7-infused surfaces arise from the anisotropic nature of the LC and transient changes in LC orientation beneath the droplets that lead to changes in droplet adhesion (droplets of DI water placed on surfaces previously exposed to aqueous SDS also slid rapidly (≈5 s), suggesting that any changes promoted by interactions with SDS-containing droplets are transient). The results of experiments using E7-infused SLIPS maintained at 70° C. (well above the nematic/isotropic transition temperature (≈60° C.) of E7) provide additional support for this hypothesis. As shown in FIG. 3 (B) (white bar), droplets of aqueous SDS (at $0.4 \times 10^{-3}$ M) slid down surfaces infused with isotropic LC over a period of ≈10 s, a time significantly shorter than that observed on surfaces infused with LC in the nematic phase (≈49 s) and similar to that observed for SDS-containing droplets on surfaces infused with silicone oil.

The results of additional experiments reveal that the sensitivity of droplet mobility to the presence of SDS also extends to the presence of other amphiphiles. For example, 10 µL droplets containing $0.4 \times 10^{-3}$ M DTAB (a cationic surfactant with a tail length identical to that of SDS) were observed to exhibit sliding times similar to those of droplets containing SDS (≈49 s; FIG. 3 (B)). Experiments using droplets containing HTAB, a cationic surfactant with a tail length four carbons longer than that of DTAB, demonstrated that manipulation of both surfactant tail length and concentration can also be used to manipulate sliding behaviors. Droplets containing $0.4 \times 10^{-3}$ M HTAB, for example, did not slide down LC-infused surfaces at tilt angles of 13° (not shown). However, droplets containing $25 \times 10^{-6}$ M HTAB slid down these surfaces over a period of ≈96 s (FIG. 3 (B); a time that is significantly longer than that required for droplets of DTAB, at a concentration 16 times higher ($0.4 \times 10^{-3}$ M), to slide the same distance). These results are consistent with the view that interactions between the amphiphile and the LC play an important role in governing sliding behaviors.

These results also demonstrate that these LC-infused surfaces can be used to report the presence of bacterial endotoxin, a highly toxic polysaccharide-based amphiphile, in aqueous droplets (Lin et al., Science (2011), 332:1297). As shown in FIG. 3 (B), droplets containing very low concentrations of LPS ($77 \times 10^{-12}$ M) slid down E7-infused surfaces over ≈93 s, a time substantially longer than that exhibited by droplets of DI water. Overall, this sensitivity of mobility to droplet compositions provides new opportunities to tune droplet behaviors (e.g., by manipulation of surfactant structure or concentration) and provides a basis for the sensing and naked-eye detection of aqueous analytes using slippery surfaces (e.g., by characterizing changes in droplet sliding velocities as a function of analyte concentration). The use of this "sliding" platform can therefore be used to qualitatively or quantitatively detect the presence of environmental analytes and toxins. These results using LC-infused SLIPS also provide opportunities to design slippery surfaces that could permit active and external control over droplet adhesion and mobility.

Example 4

Figure 4:
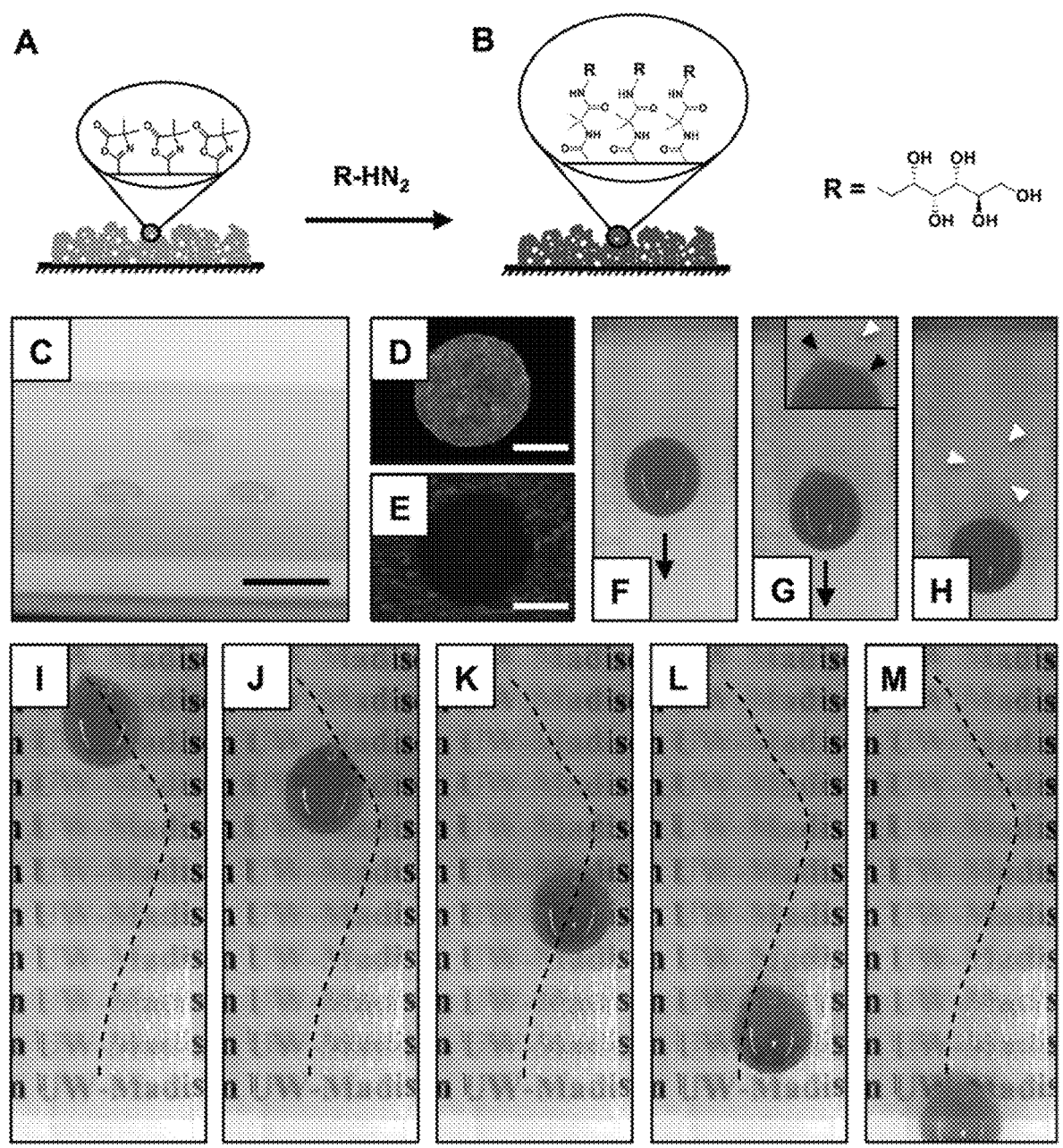
FIGS. 4. A and B) Schematic of functionalization of reactive multilayers (A) with D-glucamine to create a porous matrix presenting hydroxyl functionality (B). C) Selective transfer of an aqueous solution of fluorescein onto three sticky patches patterned by selective deposition of glucamine (followed by treatment of surrounding regions with decylamine and infusion of oil; scale=2 mm). D and E) Fluorescence microscopy images reveal aqueous fluids to be confined within glucamine-functionalized spots (D; scale=500 μm) and that sticky regions were devoid of oil (E; oil; scale=500 μm). F-H) Images showing samples of fluid captured from actively sliding drops using patterned sticky patches (white and black arrowheads show samples of fluid that have or have not yet broken free, respectively, as the droplet slides over three sticky patches). I-M) Series of images showing guided control over the in-plane path of a water droplet as it slides down the surface of a SLIPS-coated glass slide patterned with 13 strategically placed sticky spots; the dotted line traces the locations of the sticky spots and shows the non-linear sliding path.

Finally, the chemical reactivity of the multilayers described herein can be used to functionalize and spatially pattern the surfaces and the bulk of these coatings with a variety of functionality—ranging from hydrophobic, as demonstrated above (FIG. 1 (A)), to highly hydrophilic—by treatment with strategically selected primary amines (Manna et al., Adv. Funct. Mater. (2015), 25:1672; and Manna et al., Adv. Mater. (2012), 24:4291). This feature can be exploited to design SLIPS with patterned features that exclude infused oils and, as a result, create "sticky" patches (or "STICKS") that are wet by aqueous media. To demonstrate proof-of-concept, a porous multilayers spatially patterned was used by treatment with small aqueous droplets containing the hydrophilic molecule D-glucamine (FIGS. 4 (A) and (B); azlactone groups in surrounding areas were then functionalized with decylamine prior to infusion with oil). FIG. 4 (C) shows a SLIPS-coated surface patterned with three sticky patches after immersion and removal from an aqueous solution of the fluorophore fluorescein. This image reveals the patterned "STICKS" to capture aliquots of aqueous solution, and that patterning does not compromise the slippery character of the surrounding surface. Experiments using patterned SLIPS infused with silicone oil containing Nile red dye revealed the patterned regions to be devoid of oil (FIG. 4 (E); as determined by fluorescence microscopy) and that the capture of aqueous fluid was confined strictly to the patterned patches (FIG. 4 (D)).

Figure 14:
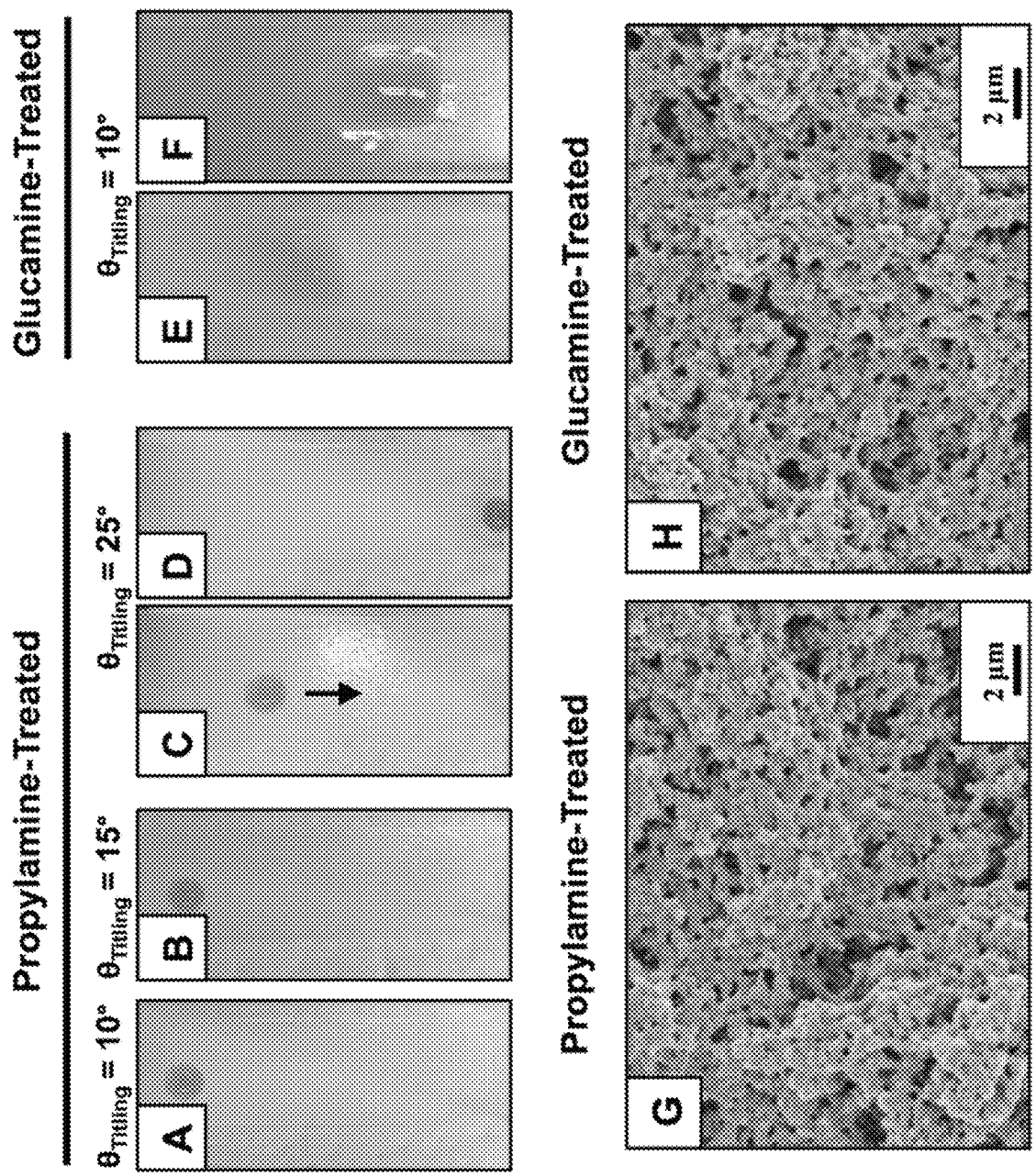
FIG. 14. A-F) Digital images showing the influence of chemical functionalization of the porous multilayer matrix on the sliding behaviors of aqueous droplets; experiments were performed using reactive multilayers fabricated on planar glass slides and functionalized by treatment with n-propylamine and D-glucamine and then infused with silicone oil. A-D) Behavior of an aqueous droplet of TMR (10 μL) on a propylamine-functionalized multilayer infused with silicone oil at tilt angles of 10°, 15°, or 25°; the droplet remained stationary and did not slide until the tilt angle was greater than 15°, a value that is greater than that observed on multilayers functionalized with n-decylamine (which exhibited tilt angles as low as ≈1°). E-F) Image showing the behavior of an aqueous droplet of TMR (10 μL) placed on a glucamine-functionalized multilayer infused with silicone oil; the droplet was observed to at least partially displace the oil and spread readily on the surface of the coating. G-H) SEM images showing porous multilayers functionalized post-fabrication by treatment with propylamine (G) and glucamine (H).

Control over the "stickiness" of SLIPS-coated surfaces can also be achieved by functionalizing PEI/PVDMA multilayers with hydrophobic n-alkanes shorter and less hydrophobic than n-decylamine. For example, infusion of silicon oil into films functionalized with n-propylamine resulted in SLIPS with higher contact angle hysteresis (≈20°) and, thus, significantly larger critical sliding angles relative to SLIPS designed using decylamine-functionalized multilayers (see FIG. 14). Control over the sizes, numbers, and relative locations of sticky patches on patterned SLIPS provided opportunities to capture samples of aqueous fluids from sliding droplets (FIG. 4 (F)-(H)), temporarily halt or completely arrest the motion of sliding droplets, and promote the transfer and mixing of fluids from multiple different sliding droplets. Provided that droplets are sufficiently large compared with the spacing between sticky patches, this approach can also be used to control the velocities and guide the in-plane trajectories of aqueous droplets as they slide along planar surfaces (e.g., along prescribed, non-linear sticky-patch paths; FIG. 4 (I)-(M)).

The work reported here addresses challenges related to the fabrication and chemical functionalization of SLIPS on complex surfaces, and provides tools for tuning interfacial properties and manipulating the behaviors of fluids in contact with this emerging class of soft materials.

Example 5

The following section describes the materials and procedures used in the above examples.

Materials.

2-Vinyl-4,4-dimethylazlactone (VDMA) was obtained from Dr. Steven M. Heilmann (3M Corporation, Minneapolis, Minn.). Poly(2-vinyl-4,4-dimethylazlactone) (PVDMA) was synthesized by free-radical polymerization of VDMA as described previously (Buck et al., Chem. Mater., 2010, 22:6319).

Branched poly(ethylene imine) (BPEI; MW~25,000), propylamine, n-decylamine (95%), acetone (HPLC grade), tetrahydrofuran (THF, HPLC grade), sodium dodecyl sulfate (SDS), dodecyltrimethylammonium bromide (DTAB), hexadecyltrimethylammonium bromide (HTAB), lipopolysaccharide from E. coli O127:B8 (LPS), dichloroethane (DCE), carbon tetrachloride (CCl4), dibromomethane (CH2Br2), magnesium sulfate, calcium chloride, and silicone oil were purchased from Sigma Aldrich (Milwaukee, Wis.). D-Glucamine (>95%) was purchased from TCI America (Portland, Oreg.). Tomato ketchup was obtained from the H. J. Heinz Company (Pittsburgh, Pa.). Glycerol was purchased from Fisher Chemicals (New Jersey, USA). Glass microscope slides were purchased from Fischer Scientific (Pittsburgh, Pa.). Thin sheets of poly(ethylene terephthalate) film (PET; 0.004 in. thick) were purchased from McMaster Carr. Stainless steel wire meshes were obtained from MSC Industrial Supply Co. (Melville, N.Y.). Aluminum foil was obtained from Reynolds Consumer Products, LLC (Richmond, Va.). Filter paper was obtained from Whatman (Maidstone, England). The thermotropic liquid crystal E7 was purchased from Licristal, Japan. Sodium chloride (NaCl) and magnesium chloride (MgCl2) were obtained from Fisher Scientific. Coconut oil was obtained from Nihar Naturals, India and canola oil was obtained from Kirkland, Canada and olive oil was obtained from Filippo Berio (Italy). All chemicals were used as received without further purification unless otherwise noted.

General Considerations.

Compressed air used to dry samples was filtered through a 0.2 μm membrane syringe filter. Scanning electron micrographs were acquired using a LEO 1530 scanning electron microscope at an accelerating voltage of 3 kV. Samples were coated with a thin layer of gold using a gold sputterer operating at 45 mA under a vacuum pressure of 50 mTorr for 40 s prior to imaging. Measurements of film thickness were made by characterizing the cross-sections of films using SEM. Cross-sectional images were acquired at several different locations (typically 4) across the edge of a film, and 25 individual measurements of thickness were made across each edge; values of film thickness are presented as an average (with standard deviation) of these 100 measurements. Digital pictures were acquired using a Canon PowerShot SX130 IS digital camera. Contact angles were measured using a Dataphysics OCA 15 Plus contact angle goniometer at ambient temperature with 10 μL of deionized water. Artificial seawater was prepared by mixing 26.73 g of NaCl, 2.26 g of MgCl$_2$, 3.25 g of MgSO$_4$, and 1.12 g of CaCl$_2$ in 1.0 L of deionized water. Unless otherwise noted, all experiments were conducted at ambient room temperature (~23° C.). Experiments to characterize the behaviors of aqueous droplets on LC-infused surfaces at 70° C. were performed by pre-heating a hot plate (tilted at an angle of 13°) to 70° C., placing SLIPS-coated glass substrates in contact with the surface of the hot plate, and allowing the temperature of the coated substrate to equilibrate for 1 hour.

Covalent Layer-by-Layer Fabrication of Porous Polymer Multilayers.

PEI/PVDMA multilayers were deposited on glass substrates using the following general procedure: (i) substrates were submerged in a solution of BPEI (20 mM in acetone with respect to the polymer repeat unit) for 20 s; (ii) substrates were removed and immersed in an initial acetone bath for 20 s followed by a second acetone bath for 20 s; (iii) substrates were submerged in a solution of PVDMA (20 mM in acetone with respect to the polymer repeat unit) for 20 s; and (iv) substrates were removed and rinsed again using the procedure outlined under step (ii). This cycle was repeated 35 times to fabricate porous polymer multilayers consisting of 35 BPEI/PVDMA layer pairs (or 'bilayers'). The concentrations of the polymer solutions were maintained by addition of acetone as needed to compensate for solvent evaporation after every dipping cycle. All other substrates used in this study (glass tubes, aluminum foil, PET film, PTFE tubes, wire meshes, and filter paper) were also coated using this protocol. Multilayers were characterized and used in subsequent experiments immediately or dried under a stream of filtered, compressed air and stored in a vacuum desiccator until use. All films were fabricated at ambient room temperature.

Chemical Functionalization of Porous Polymer Multilayers.

Porous polymer multilayers containing unreacted azlactone groups were functionalized by treatment with various hydrophobic (decylamine or propylamine) and hydrophilic (glucamine) primary amine-containing small molecules. Solutions of decylamine and propylamine (20 nmM) were prepared in THF, and solutions of glucamine (20 mM) were prepared in either DMSO or PBS buffer. Amine-reactive multilayers were then immersed in these solutions at room temperature for two hours to install hydrophobic or hydrophilic functionality over large areas (Manna et al., Adv. Mater., 2012, 24:4291). Functionalized films were then rinsed with THF or DMSO and acetone and dried with filtered air.

Infusion of Oils into Porous Polymer Multilayers.

Hydrophobic multilayers (5 cm×1 cm) were infused with lubricating liquids (silicone oil, canola oil, olive oil, coconut oil, motor oil, or the thermotropic liquid crystal E7) using the following general protocol. A droplet of 5 μL of oil was placed onto the film and spread over the surface using weighing paper. After two minutes, excess oil was removed from the surface by soaking it into weighing paper.

Characterization of Physical and Chemical Robustness of Liquid-Infused Coatings.

All tests used to characterize the integrity of liquid-infused multilayers after exposure to physical abuse and chemically harsh conditions were performed using decylamine-treated multilayers. For experiments to characterize the influence of scratching on slippery properties, syringe needles were dragged manually across the surfaces of oil-infused coatings to create full-thickness scratches. For experiments to characterize the stability of slippery coatings upon exposure to rapidly flowing water, oil-infused coatings were exposed to a stream of water having a flow rate of 100 mL/s for 15 min. For experiments to characterize the influence of immersion in aqueous environments on stability, oil-infused films were immersed in water, 1.0 M NaCl solutions, artificial seawater, and samples of locally-sourced lake eutrophic water (Lake Mendota, Madison, Wis.) for two months; film properties were characterized at regular time intervals. The influence of freezing was characterized by placing a glass slide coated in oil-infused multilayers in deionized water and placing the whole system in a freezer for six hours; the resulting block of ice was thawed to room temperature and the interfacial properties of the oil-infused films (e.g., water sliding angles) were characterized; freezing/thawing/characterization cycles were performed 10 times. Substrates exposed to steam were autoclaved for 45 minutes at 121° C. using an Allen-Bradley Panel View Plus 600 System. Bending and creasing of slippery, liquid-infused multilayers fabricated on soft and flexible substrates (PET) was accomplished manually by repeatedly bending (~50 times) and then finally permanently creasing the substrates using moderate pressure.

Separation of Oil/Water Mixtures using Porous Meshes Coated with Liquid-Infused Multilayers.

Stainless steel wire meshes (1.5 cm×4 cm; wire diameter ~90 µm; pore size=126.3±3.5 µm) coated with decylamine-functionalized multilayers were infused with conventional automotive motor oil, placed over the open mouth of a laboratory beaker, and maintained at a tilted angle of ~2° with respect to the mouth of the beaker by supporting one side of the mesh using a glass chip (see FIG. 9 (E). A mixture (3:2, v/v) of motor oil and water (or other aqueous fluids) was then poured onto the coated mesh. Oil that passed through the mesh was collected in the beaker; water was observed to slip off of the surface of the oil-infused mesh, and was collected in a secondary container (see FIGS. 9 (F) and (G)).

Selective and Guided Transfer of Water on Slippery, Oil-Infused Multilayers Patterned with Hydrophilic Patches.

Reactive porous polymer multilayers, fabricated as described above, were patterned with small hydrophilic domains by placing droplets of aqueous solutions of glucamine (e.g., 0.5 µL of a 20 mg/mL glucamine solution in PBS buffer, adjusted to pH 9.0) for 10 minutes, as previously described (Manna et al., Adv. Mater., 2012, 24:4291). These chemically patterned samples were then immersed in n-decylamine using the procedure described above to react with remaining azlactone functionality and render the remainder of the surrounding regions of the films hydrophobic. To characterize the fidelity of patterning and the behavior of liquid lubricants in the hydrophilic glucamine-patterned regions after oil infusion, samples were infused with silicon oil containing Nile red (an oil-soluble, water immiscible dye). The oil infused patterned substrate was then submerged in an aqueous solution of fluorescein (20 µg/mL) for several seconds and removed. Visual inspection and fluorescence microscopy were then used to characterize the locations of red (Nile red) and green (fluorescein) signal in the hydrophobic and hydrophilic patterned regions of the films. Experiments to investigate (i) the ability of patterned spots to capture samples of sliding aqueous droplets and (ii) the ability of networks or 'tracks' of multiple small hydrophilic spots to guide the gravity-driven transfer of larger water droplets were conducted using 55 µL droplets of an aqueous TMR solution and chemically patterned substrates maintained at an inclination angle of 5°.

Example 6

Functionalization of Azlactone-Containing Polymer Multilayers

As described above, polymers bearing amine-reactive azlactone functionality can be used to drive reactive layer-by-layer assembly with polymers that contain primary amines. Azlactones react rapidly, through ring-opening reactions, with primary amines under mild conditions (Buck et al., Polymer Chemistry (2012), 3 (1):66; and Heilmann et al. Journal of Polymer Science, Part A: Polymer Chemistry (2001), 39 (21): 3655), leading to unique and stable amide/amide-type crosslinks between polymer chains. Residual azlactone functionality in resulting PEI/PVDMA multilayers can be used as reactive handles for further functionalization by treatment with any of a broad range of readily available amine-based nucleophiles to impart a new surface and bulk properties, such as hydrophobicity of the multilayer or interaction with an oils as part of SLIPS, through the creation of unique and chemically stable amide/amide-type bonds.

Additionally, the surface and bulk properties of azlactone-containing materials can also be altered using other classes of non-amine-based nucleophiles (see Scheme 1). For example, azlactone groups are understood to react with primary alcohols and thiols under certain conditions such as in the presence of a catalyst and at higher temperatures (Heilmann et al. Journal of Polymer Science, Part A: Polymer Chemistry (2001), 39 (21): 3655; Schmitt et al., Adv. Healthcare Mater. (2015), 4(10):1555; Schmitt et al., Biomacromolecules (2016), 17(3):1040; Heilmann et al., J. Polym. Sci., Polym. Chem. Ed. (1984), 22 (5):1179; Rasmussen et al., Makromol. Chem. Rapid Commun. (1984), 5 (2):67; Heilmann et al., Tetrahedron (1998), 54(40):12151; and Pereira et al., Tetrahedron (2014), 70(20):3271).

The use of these nucleophiles to design new materials is far less developed than approaches that exploit the reactivity of azlactones with more nucleophilic primary amines. Strategies for the rapid and robust functionalization of azlactone groups in polymer assemblies using primary alcohols and thiols could be broadly useful in at least two ways. First, such methods would substantially increase the pool of commercially or readily available molecules that is available for post-fabrication functionalization (and, thus, expand the range of new properties that could be imparted to azlactone-containing assemblies). Second, the reaction of azlactones with primary alcohols and thiols results in the formation of unique amide/ester- and amide/thioester-type bonds that, in contrast to the amide/amide bonds formed by reactions with primary amines, can be hydrolyzed under relatively mild conditions. Thus, a functionalized azlactone layer (not hydrolyzed) can be designed to be hydrophobic while the functionalized azlactone layer which has been hydrolyzed to break amide/ester- or amide/thioester-type bonds can be designed to be relatively hydrophilic.

Methods for the functionalization of surfaces and coatings using these labile and stimuli-responsive linkages thus provide new approaches to the design of surfaces with dynamic or stimuli-responsive properties.

Functionalization of azlactone-containing PEI/PVDMA multilayers using primary alcohol and thiol-containing nucleophiles is thus provided. Alcohol- or thiol-containing compounds can react uniformly and extensively with the residual azlactone functionality in these materials when an organic catalyst is used, and the properties of these compounds (e.g., whether they are hydrophobic or hydrophilic, etc.) can be used to dictate important interfacial properties and pattern useful surface features. It is further demonstrated that the amide/ester and amide/thioester groups that result from these new reactions can be cleaved under mild conditions, leading to dynamic and stimuli responsive materials that can undergo stimuli-responsive changes in hydrophobicity and interactions with oils. The post-fabrication conversion of installed thioester groups can also be used to create acylhydrazine functionality that can react through 'click-like' reactions with aldehydes (Xin et al., Polymer Chemistry (2012), 3(11):3045; and Kool et al., Journal of the American Chemical Society (2013), 135(47):17663) to anchor new surface features through acid-responsive imine bonds. These results expand the range of chemical functionality and new functions that can be imparted to azlactone-containing materials beyond those that can be attained by functionalization using primary amines. The strategies reported here, demonstrated using model polymer-based reactive multilayer coatings, can also prove useful for the design of new materials based on other types of azlactone-functionalized polymers, assemblies, and coatings.

Functionalization of Polymer Multilayers Using Amine, Alcohol, and Thiol-Containing Nucleophiles.

PEI/PVDMA multilayers were fabricated on glass substrates using the general procedure described above. Films were then functionalized with nucleophiles using the following general procedure. Treatment with pyrenebutanol and pyrene (serving as a control) was performed by immersing a 10-bilayer film (0.9×1 cm) on a glass substrate in 1.5 mL of the desired fluorophore solution (40 mg/mL in DCE) in a glass vial, followed by the addition of 2 µL of DBU. The vial was capped, sealed with parafilm, and left on a shaker plate overnight at room temperature. Films were removed and rinsed copiously with DCE, and then placed in large vials containing fresh DCE rinse solution for several days in order to remove any non-specifically adsorbed fluorophore and the DBU catalyst. The rinse solution was changed several times each day. Films were finally rinsed with ~25 mL each of DCM, methanol, water, and acetone, and then dried in a stream of compressed air.

Decanol and decanethiol treatments were performed in a similar manner by immersing films (~0.9 cm×3 cm) in ~4 mL of the desired nucleophile solution (1:1 wt/wt in DCE) in a glass vial followed by addition of 54 µL of DBU. The vial was capped, sealed with parafilm, and left on a shaker plate overnight. Films were rinsed copiously with DCE and then DCM before being placed in DCM rinse vials for several days, as above. Decylamine and hydrazine functionalization reactions were performed by immersing a film (~0.9 cm×3 cm) in a ~4 mL solution of either decylamine (20 mg/mL in THF) or anhydrous hydrazine (20 mg/mL in MeOH) overnight and then rinsing with THF or MeOH, respectively, and then acetone, before drying in a stream of compressed air.

Hydrolysis of Ester and Thioester Bonds in Functionalized Films.

Experiments designed to characterize the hydrolysis of the ester bonds in multilayers functionalized using decanol were performed by placing small droplets of aqueous NaOH (0.05 M) onto the surface of a film and incubating it in a humid chamber for pre-determined periods of time. The NaOH droplet was rinsed from the surface of the film using Millipore water and then subsequently with acetone before drying in compressed air. To facilitate imaging, newly created hydrophilic spots on these films were loaded selectively with TMR by submersion of the entire film into an aqueous solution of the dye (~0.05 mg/mL) for ~2 seconds. To demonstrate the reactivity of thioester bonds in decanethiol treated films, samples (0.9×1 cm) were immersed in 1.5 mL of hydrazine solution (20 mg/mL in MeOH) at 50° C., removed at pre-determined time intervals, rinsed in MeOH and acetone, and then dried in compressed air prior to characterization.

Reversible Reactions of Imine Bonds in Hydrazine-Functionalized Multilayers.

Films functionalized by treatment with hydrazine were treated with octylaldehyde (20 mg/mL in MeOH) for 1 hour at room temperature and then rinsed copiously with MeOH and acetone before being dried in a stream of compressed air. These superhydrophobic films were cut to desired sizes (1×1 cm) and immersed in 2 mL of a 1 M HCl solution (1:1 $H_2O$:THF, v/v) overnight at room temperature. The resulting hydrophilic films were then removed and rinsed copiously with THF, water, and acetone before being dried in a stream of compressed air for contact angle analysis. Experiments were also performed without HCl by placing films into solutions of 1:1 v/v $H_2O$:THF and removing after pre-determined periods of time. This process was repeated several times to characterize the reversibility of the imine bond formation/hydrolysis reaction.

Functionalization of Azlactone-Containing Multilayers Using Alcohol-Based Nucleophiles.

The reactivity of the residual azlactone groups in PEI/PVDMA multilayers with primary alcohol-based nucleophiles was characterized. These initial experiments were conducted using PEI/PVDMA multilayers 10 bilayers (~160 nm) thick and pyrenebutanol as a model fluorescent primary alcohol to facilitate characterization. Prior to experiments using azlactone-containing multilayers, studies were conducted using solutions of pyrenebutanol and PVDMA to identify reaction conditions that lead to efficient coupling. Past studies demonstrate that reactions between azlactones and alcohols do not occur substantially in the absence of a catalyst, but that these reactions can be promoted by catalytic amounts of trifluoroacetic acid or strong amidine bases such as 1,8-diazabicycloundec-7-ene (DBU) (Heilmann et al., Journal of Polymer Science, Part A: Polymer Chemistry (2001), 39(21): 3655; Pereira et al., Tetrahedron (2014), 70(20): 3271; and Sun et al., Journal of Controlled Release (2010), 148(1):91). DBU was selected as a catalyst for these studies because this approach is more general and because it can also be used to promote reactions between azlactones and thiols (trifluoroacetic acid can catalyze the addition of alcohols to azlactone groups, but does not promote reactions using thiols). The addition of pyrenebutanol to solutions of PVDMA in the presence of DBU (0.05 eq. pyrenebutanol, 0.1 eq. DBU with respect to pyrenebutanol) yielded random copolymers containing both reactive azlactone functionality and pyrenebutanol-based side chains attached to the backbone through amide/ester linkages, as characterized by $^1$H NMR spectroscopy and gel permeation chromatography.

Modification of Interfacial Properties Using Alcohol- and Thiol-Based Nucleophiles.

Previous experiments demonstrate that the surface energies and wetting behaviors of native (azlactone-containing) PEI/PVDMA films can be permanently modified (through the creation of amide/amide-type bonds) by treatment with primary amines functionalized with hydrophobic or hydrophilic groups. Those prior experiments reveal that when these covalent modifications are made to multilayers possessing nano- and microscale topographic features, this approach can also be used to design films that are superhydrophobic, or extremely non-wetting to water [superhydrophobic surfaces are defined here having advancing water contact angles (WCAs)>150°, with low water roll-off angles]. The functionalization of nanoporous PEI/PVDMA films~3.5 μm thick by reaction with n-decylamine yielded an increase in WCA from 135.6° (±1.9°) (FIGS. 15 (A) and (E) for native, azlactone-functionalized films) to 158.3° (±1.7°) (FIGS. 15(B) and (F)).

Figure 15:
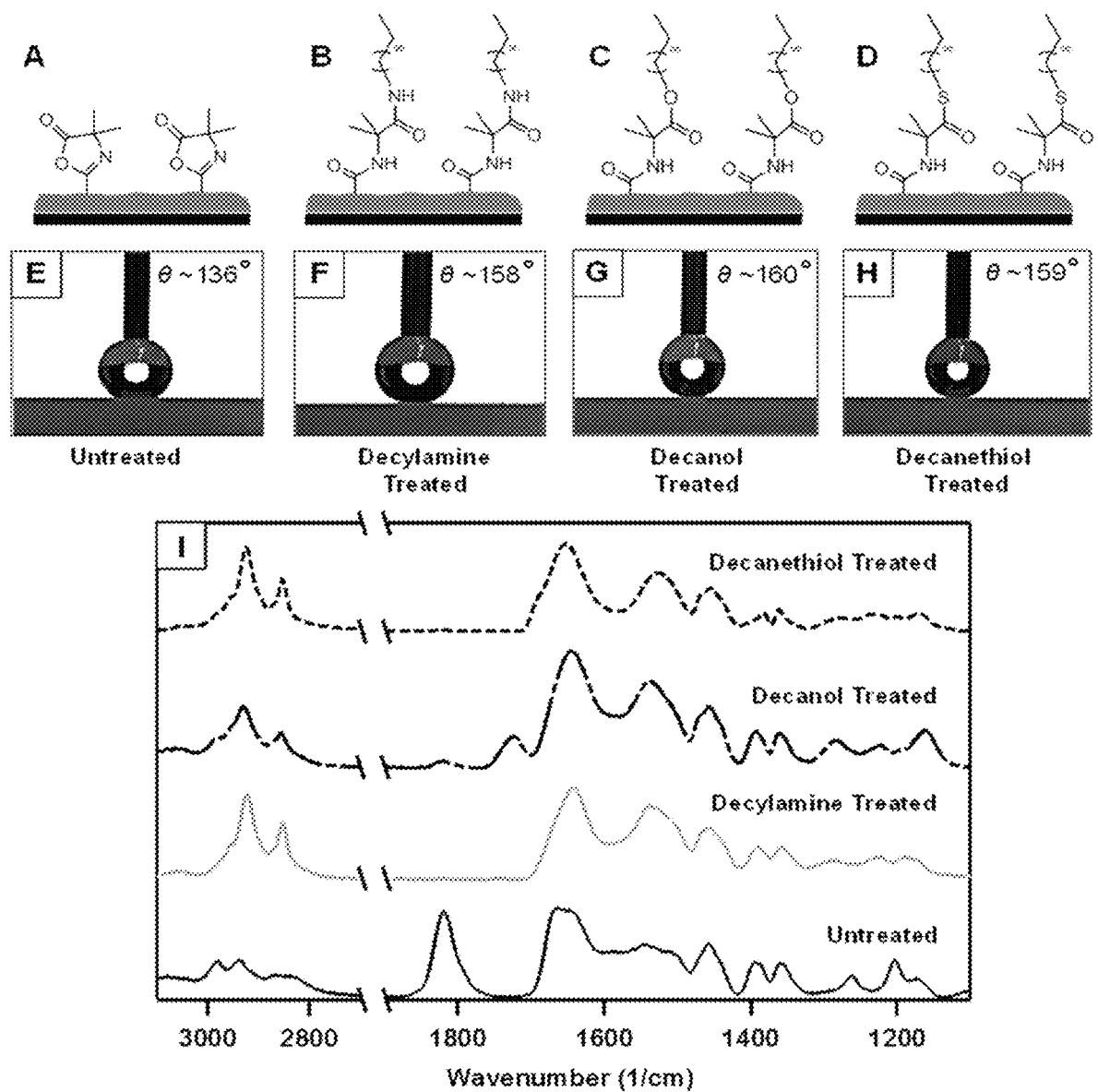
FIG. 15. Chemical structures representing PEI/PVDMA LbL films, with panel (A) showing an azlactone-containing, unfunctionalized film, and films functionalized with decylamine (B), decanol (C) and decanethiol (D). Representative advancing WCA measurements for the corresponding films in (A)-(D) are provided in (E)-(H). I) provides ATR IR thin film spectra for the unfunctionalized film (azlactone C=O carbonyl stretch, 1819 $cm^{-1}$) and decylamine, decanol or decanethiol functionalized films, showing complete or near complete consumption of the azlactone peak.

The images in FIGS. 15 (C)-(D) and (H)-(G) reveal that superhydrophobicity can also be achieved by the DBU-catalyzed reaction of residual azlactones with the hydrophobic alcohol n-decanol (WCA=160.3±1.8°; panel (G)) and the hydrophobic thiol n-decanethiol (WCA=159.0±1.6°; panel (G)). These decanol- and decanethiol-functionalized films were uniformly superhydrophobic across the entirety of the material, with properties and behaviors that were both quantitatively and qualitatively similar to those exhibited by decylamine-functionalized films when placed in contact with or immersed in water.

FIG. 15 (I) shows representative ATR IR spectra of an untreated (azlactone-containing) PEI/PVDMA film and decylamine-, decanol-, and decanethiol-treated films used in the experiments above. The IR spectrum of the untreated film exhibited a cyclic carbonyl C=O stretch characteristic of residual azlactone groups at 1819 $cm^{-1}$; the two coalescing absorbance bands with peaks at 1666 $cm^{-1}$ and 1646 $cm^{-1}$ correspond to the C=N functionality in the azlactone ring and the C=O stretch of amide bonds that make up the crosslinks of the film, respectively. For films treated with decylamine, the peak corresponding to the azlactone functionality at 1819 $cm^{-1}$ was completely consumed, suggesting exhaustive reaction of the azlactone groups with the incoming amine-based nucleophile and consistent with the results of past studies. For films treated with decanol, the intensity of the azlactone carbonyl stretch at 1819 $cm^{-1}$ was also substantially reduced, and a carbonyl C=O stretch at 1724 $cm^{-1}$ appeared, consistent with the formation of ester bonds upon the reaction of the azlactone groups with this alcohol-based nucleophile. Finally, for films treated with decanethiol, the azlactone peak was also consumed and close inspection of the data reveals a shoulder on the amide C=O stretch (near 1652 $cm^{-1}$) that were attributed to the C=O carbonyl stretching of thioester functionality. These results, when combined, are consistent with the ring-opening of residual azlactone rings by these alcohol- and thiol-based nucleophiles under these DBU-catalyzed conditions.

The results of additional experiments demonstrated that, whereas the superhydrophobicity of decylamine-treated films can be maintained for long periods in aqueous environments, the extremely non-wetting behaviors of decanol- and decanethiol-treated films could be permanently erased and eliminated by exposure to aqueous analytes that cleave ester and thioester bonds. For these experiments, PEI/PVDMA films fabricated on amine-functionalized poly(ethylene terephthalate) (PET) substrates were used to improve stability at the film/substrate interface and reduce the likelihood of film delamination.

Figure 16:
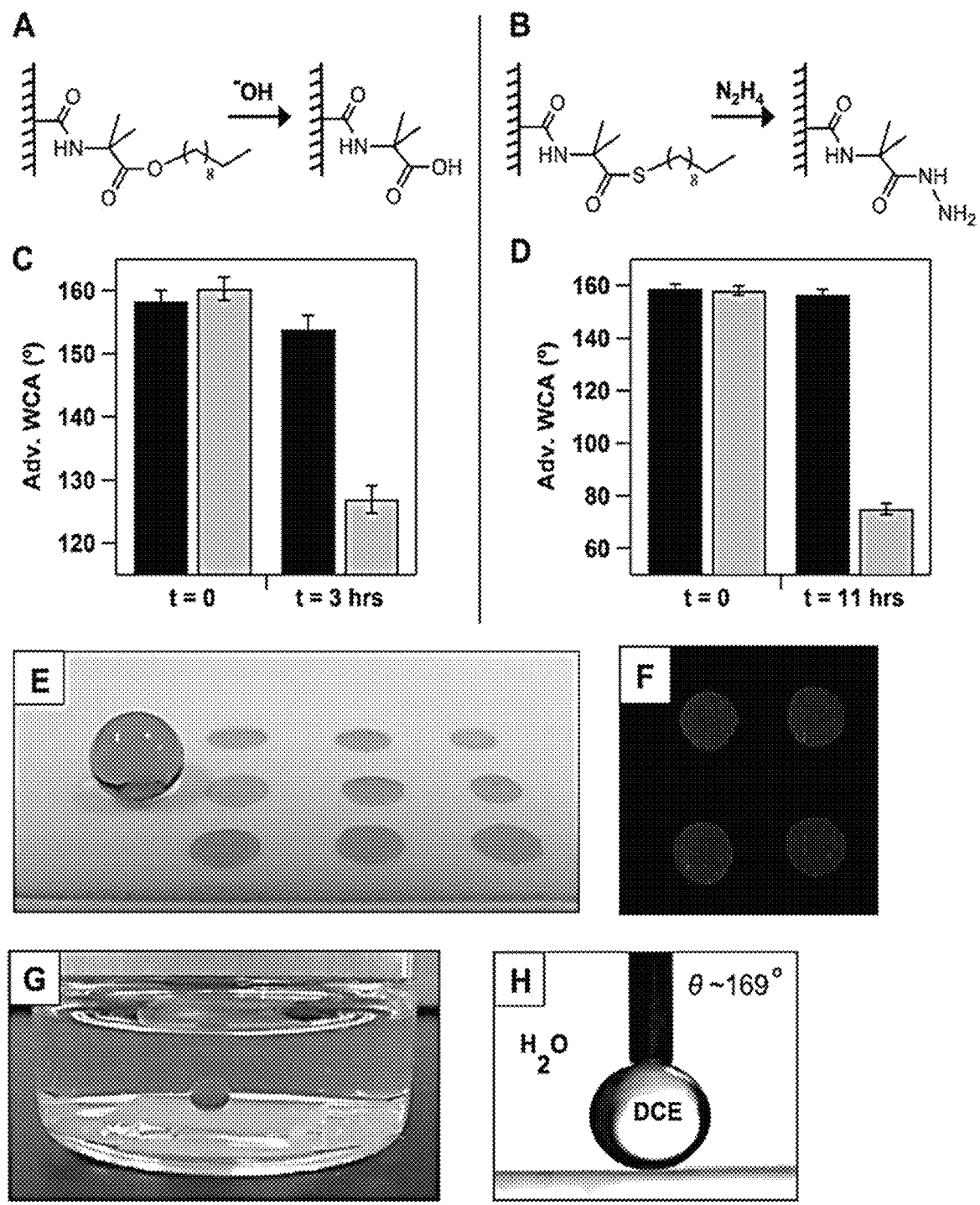
FIG. 16. Chemical structures for PEI/PVDMA films functionalized with decanol (A), and the result after treatment by hydroxyl ions, and films functionalized with decanethiol (B), and the result after treatment with hydrazine. C) change in the advancing WCA of decanol functionalized films are shown in (gray bars) and decylamine functionalized films (black bars) upon exposure to 50 mM aqueous NaOH. D) change in the advancing WCA of decanethiol functionalized films (gray bars) and decylamine functionalized films (black bars) upon exposure to hydrazine. E) digital picture of a 3×3 array of hydrophilic spots patterned by hydrolysis with aqueous base onto a decanol functionalized film; a large droplet of water placed nearby beads up on the untreated and still superhydrophobic region. F) fluorescence micrograph of a 2×2 array, prepared the same way as in (E), after loading the hydrophilic spots with the fluorescent dye TMR. G) digital image of an oil (dichloroethane, DCE) droplet on the surface of an underwater-superoleophobic film (~1×1 cm) submerged in a vial underwater; the film was prepared as in (B). H) advancing oil contact angle underwater. Water and oil were dyed to aid visualization.

In an initial series of experiments, the wetting behaviors of decylamine- and decanol-treated films exposed to aqueous base were characterized, with the reasoning that the hydrolysis of ester bonds would reveal hydrophilic carboxylic acid groups (e.g.. FIG. 16 (A)) and result in large reductions in WCAs. FIG. 16 (C) shows the results of an experiment in which a large aqueous droplet of 50 mM NaOH was placed onto the surfaces of both decylamine- and decanol-treated films in a humid environment for ~3 hours at room temperature. Inspection of these results reveals a large reduction in the WCA of the decanol-treated film (from ~160° to ~126.9±2.2°; FIG. 16 (C), gray bars) in the areas of the film treated with aqueous base. In contrast, the WCA of the decylamine-treated films remained largely unaffected under these conditions (FIG. 16 (C), black bars). These results are also consistent with the hydrolysis of the ester bonds of decanol-treated materials. The hydrolyzed regions of the decanol-treated films were rapidly and uniformly wet when contacted with water, whereas surrounding areas that were not treated remained superhydrophobic and were jacketed by a layer of air, as is typical of superhydrophobic surfaces in the Wenzel-Cassie state, when immersed in water. This observation suggests new approaches to the chemical patterning of superhydrophobic materials and provides a basis for the design of new surfaces with patterned contrasts in wettability. The selective deposition of small (10 μL) droplets of aqueous base were used to pattern a small array of hydrophilic spots distributed within a superhydrophobic background (FIG. 16 (E); small droplets of colored water show the locations of the hydrophilic spots; a larger droplet reveals the maintenance of superhydrophobicity in surrounding, untreated areas). These arrays of hydrophilic spots could also be used to directly capture and position small samples of water by direct dipping into aqueous solutions without substantial wetting or contamination of the surrounding superhydrophobic surfaces (FIG. 16 (F)).

A similar series of experiments using superhydrophobic decanethiol-treated films to determine if these thioester-functionalized films could be induced to undergo changes in structure and wetting behavior in response to a specific chemical stimulus. For these experiments, hydrazine was used as a model nucleophile to attack the thioester and displace hydrophobic decyl chains (FIG. 16 (B)). FIG. 16 (D) shows the results of experiments in which decanethiol-functionalized films were treated with hydrazine over a period of ~11 hours. These results reveal a dramatic reduction in WCA from >150° to ~75.0° (±6.2°) for decanethiol-functionalized films (gray bars; results using decylamine-functionalized films treated with hydrazine were again stable and did not exhibit changes in contact angle under these conditions; FIG. 16 (D); black bars). A formal loss of superhydrophobicity was also observed in decanethiol-functionalized films at shorter reaction times; for example, WCAs decreased to ~134.2° (±5.3°) after ~5 hours, suggesting that lower exposure times could be used in instances where simple transitions in wetting states are desired. These results are consistent with the hydrazine-mediated cleavage of the hydrophobic thioester groups and the installation of more hydrophilic acylhydrazine groups (FIG. 16 (B)).

The inherent nano- and microscale roughness of these superhydrophobic coatings, combined with the degree of hydrophilicity induced by treatment with hydrazine and the cleavage of hydrophobic thioester functionality, resulted in films that were highly absorbent to water but extremely repellant of oils when placed in aqueous environments (a phenomenon known as 'underwater superoleophobicity'). FIG. 16 (G) shows a droplet of a model oil (dichloroethane, stained with a red hydrophobic dye) placed on a hydrazine-treated film submerged in water. As shown in FIG. 16 (H), this surface exhibits an underwater advancing oil contact angle of approximately 169°, indicating a transition to a robust and extremely oil repellant state (whereas the surface is fully wet by water in air). This feature, combined with the ability to chemically pattern regions of hydrophilicity on these substrates are useful for the design of new surfaces that can capture, manipulate, and guide the transport of oily substances in underwater environments.

Characterization of Reactive Acylhydrazine-Functionalized Multilayers.

Figure 17:
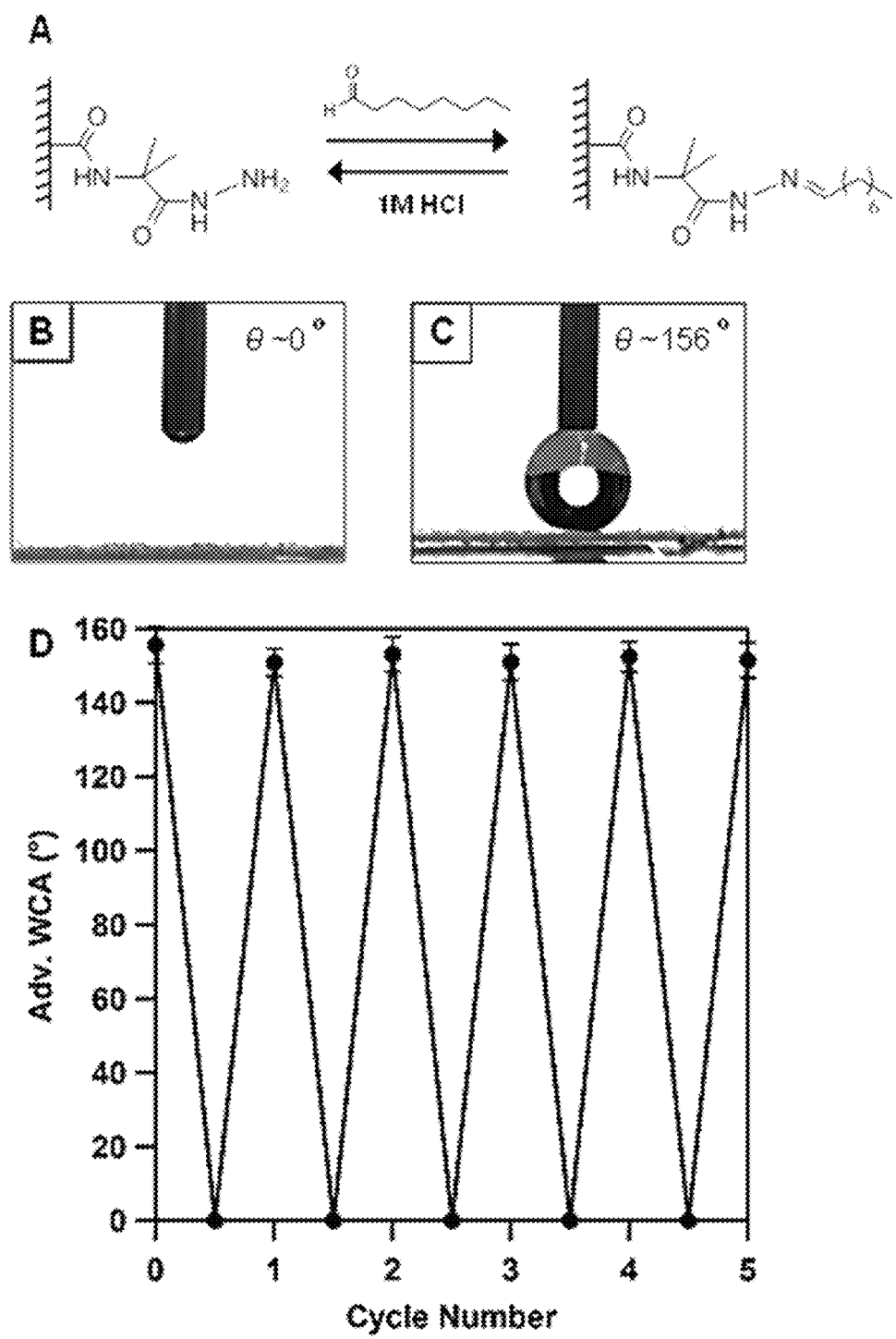
FIG. 17. A) shows chemical structure for the reaction of a PEI/PVDMA film functionalized with acylhydrazine and then octyl aldehyde (forward direction) and imine bond cleavage under acidic conditions (reverse direction). B) shows advancing WCA for the hydrophilic acylhydrazine-presenting film and for the superhydrophobic octyl aldehyde functionalized film (C). D) shows a plot showing the reversibility of the process illustrated in (A), as monitored by changes in advancing WCA. One cycle begins with the superhydrophobic octyl aldehyde film, followed by treatment with acidic media, and the subsequent return to the superhydrophobic state. Error bars represent the standard deviation of measurements obtained on three identically prepared films.

The ability to functionalize azlactone-containing films using alcohol- and thiol-based nucleophiles substantially expands the range of additional molecules that can be installed and, as described above, introduces new functionality (e.g., the introduction of chemically labile linkers) that can lead to materials with new and useful behaviors that differ substantially from those designed using primary amine-based nucleophiles. The introduction of acylhydrazine groups in the work described above—a byproduct of treatment with hydrazine to cleave surface-bound thioester functionality—could also be used as a useful reactive synthon that could further expand the range of functional groups that could be installed in these materials (i.e., by broadening the pool further, to include the immobilization of aldehyde-containing molecules; FIG. 17 (A)) and, thus, the range of functionality that can be achieved through the installation of acid-labile imine bonds and other chemically reversible groups.

To explore the feasibility of this approach, experiments were performed using nanoporous PEI/PVDMA multilayers reacted exhaustively with hydrazine (20 mg/mL in methanol, overnight). These acylhydrazine-functionalized films were superhydrophilic (they exhibited WCAs of ~0°; FIG. 17 (B)) and were extremely non-wetting to oils when submerged in water, as expected from our observations described above. These acylhydrazine-functionalized coatings were treated with octyl aldehyde to install hydrophobic octyl groups through a rapid and 'click-like' reaction that results in the formation of an acid-sensitive imine linker (20 mg/mL in methanol, 1 hour; FIG. 17 (A)). Characterization of these surfaces after octyl aldehyde treatment revealed these coatings to exhibit robust superhydrophobicity (WCA~156; FIG. 17 (C)) similar to those obtained by treatment with hydrophobic amine-, alcohol-, and thiol-based nucleophiles (e.g., FIG. 15).

The introduction of imine bonds rendered these surfaces sensitive to acidic conditions—exposure to acidic media (1.0 M HCl; 1:1 THF/H$_2$O) resulted in the cleavage of the imine bonds, the recovery of acylhydrazine functionality on the coatings, and the concurrent return of superhydrophilic surface character (WCAs)~0°) and underwater-superoleophobic behavior. Because this acid-catalyzed cleavage process regenerates acylhydrazine functionality, superhydrophobicity could be restored by re-treatment with octyl aldehyde—transitions between superhydrophobicity and superhydrophilicity/underwater superoleophobicity could be cycled reversibly at least 5 times without erosion of expected wetting behaviors (FIG. 17 (D)).

Thus, new approaches for the chemical modification of azlactone-functionalized polymer multilayers using alcohol- and thiol-based nucleophiles or by direct treatment with hydrazine are hereby provided. These methods broaden the pool of compounds available for the post-fabrication functionalization of these reactive multilayers substantially (e.g., to include molecules functionalized with alcohol, thiol, or aldehyde groups) and provide strategies for the design of thin films and surface coatings with novel amide/ester-, amide/thioester-, and amide/imine-type bonds that are, in contrast to those produced by reactions with primary amines, chemically labile and stimuli responsive. These results open the door to the design of new environmentally responsive materials and coatings, including surfaces that can promote the traceless release of covalently-immobilized molecules and coatings that undergo dynamic and predictable changes in extreme wetting behaviors, such as superhydrophobicity, superhydrophilicity, or underwater superoleophobicity, in response to environmental stimuli. The properties and behaviors of these materials could prove useful in emerging applications of special-wetting surfaces, including the design of surfaces that can capture and guide the passive transport of fluids, new materials for oil/water separation, and in areas such as controlled release, where controlled and time-dependent changes in extreme wetting behaviors could be used to control the ingress of water into a coating (and, thus, provide control over the rate at imbedded water-soluble or water-sensitive agents are released). Overall, the results of this example broaden the range of chemical functionality that can be installed in azlactone-containing multilayers, and thus also expand the range of new functions and properties that can be imparted, beyond those that can be attained by functionalization using primary amines.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that the use of such terms and expressions exclude any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

The invention claimed is:

1. A method for fabricating a nanoporous or microporous slippery liquid-infused porous surface (SLIPS) multilayer film on a substrate, wherein said multilayer film comprises one or more bilayers, said method comprising the steps of:
   a) exposing the surface of the substrate to a first solution comprising a first polymer wherein a layer of the first polymer is deposited on at least a portion of the substrate;
   b) exposing the substrate to a second solution comprising a second polymer wherein the second polymer reacts with the first polymer layer and a layer of the second polymer is deposited on, and in contact with, at least a portion of the first polymer layer, thereby forming a bilayer having nanoscale porosity or microscale porosity in the multilayer film;
   c) functionalizing at least a portion of the multilayer film to be hydrophobic; and
   d) exposing the substrate to a hydrophobic oil, selected from the group consisting of a silicone oil, a vegetable oil, a mineral oil, a thermotropic liquid crystal, and combinations thereof, wherein said oil coats at least the functionalized portion of the multilayer film and said oil at least partially fills the pores of at least the functionalized portion of said multilayer film.

2. The method of claim 1 further comprising the step of patterning the substrate so that the multilayer film is formed on a first specified portion of the substrate and a second specified portion of the substrate is not covered by the oil infused multilayer film.

3. The method of claim 2 further comprising the step of functionalizing a portion of the one or more bilayers on the first specified portion of the substrate with an amine, hydroxyl group, thiol group, or hydrazine group having the formula R—$NH_2$, R—OH, R—SH or R—$NHNH_2$, where R is hydrophobic.

4. The method of claim 2 further comprising the steps of patterning the substrate so that the multilayer film is formed on a first and third specified portion of the substrate, a second specified portion of the substrate is not covered by the oil infused multilayer film, functionalizing a portion of the one or more bilayers on the first specified portion of the substrate with an amine, hydroxyl group, thiol group, or hydrazine group having the formula R—$NH_2$, R—OH, R—SH or R—$NHNH_2$, where R is hydrophobic, and functionalizing a portion of the one or more bilayers on the third specified portion of the substrate with an amine, hydroxyl group, thiol group, or hydrazine group having the formula R—$NH_2$, R—OH, R—SH or R—$NHNH_2$, where R is hydrophilic.

5. The method of claim 1 further comprising the steps of patterning the substrate so that the multilayer film is formed on a first and second specified portion of the substrate, and functionalizing a portion of the one or more bilayers on the first specified portion of the substrate with an amine, hydroxyl group, thiol group, or hydrazine group having the formula R—$NH_2$, R—OH, R—SH or R—$NHNH_2$, where R is hydrophobic, and functionalizing a portion of the one or more bilayers on the second specified portion of the substrate with an amine, hydroxyl group, thiol group, or hydrazine group having the formula R—$NH_2$, R—OH, R—SH or R—$NHNH_2$, where R is hydrophilic.

6. The method of claim 1 wherein steps a) and b) are repeated one or more times before the substrate is exposed to the oil, where each cycle deposits a new bilayer on the substrate.

7. The method of claim 1 wherein steps a) and b) are repeated 10 or more times.

8. The method of claim 1 wherein the first polymer layer comprises a functionalized azlactone having the formula:

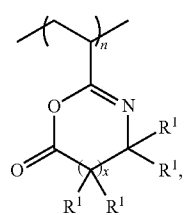

wherein x is 0 or the integers 1 or 2; and each $R^1$ is independently selected from the group consisting of: hydrogen, alkyl groups, alkenyl groups, alkynyl groups, carbocyclic groups, heterocyclic groups, aryl groups, heteroaryl groups, alkoxy groups, aldehyde groups, ether groups, and ester groups, any of which may be substituted or unsubstituted.

9. The method of claim 1 wherein the first polymer layer comprises a polymer selected from the group consisting of poly(vinyl-4,4-dimethylazlactone), poly(2-vinyl-4,4-dimethy 1-2-oxazolin-5-one), poly(2-isopropenyl-4,4-dimethyl-2-oxazolin-5-one), poly(2-viny 1-4,4-diethy 1-2-oxazolin-5-one), poly(2-vinyl-4-ethyl-4-methyl-2-oxazolin-5-one), poly(2-vinyl-4-dodecy-4-methyl-2-oxazolin-5-one), poly(2-vinyl-4,4-pentamethy lene-2-oxazolin-5-one), poly(2 -viny 1-4-methy 1-4-pheny 1-2-oxazolin-5 -one), poly(2-isopropeny-4-benzyl-4-methyl-2-oxazolin-5-one), or poly(2-vinyl-4,4-dimethyl-1 ,3-oxazin-6-one).

10. The method of claim 1 wherein the first polymer layer is poly(vinyl-4,4-dimethylazlactone).

11. The method of claim 1 wherein the second polymer layer comprises a primary amine functionalized polymer, an alcohol functionalized polymer, or a thiol functionalized polymer.

12. The method of claim 1 wherein the second polymer layer comprises an optionally functionalized polymer selected from the group consisting of polyolefins, poly(alkyls), poly(alkenyls), poly(ethers), poly(esters), poly(imides), polyamides, poly(aryls), poly(heterocycles), poly(ethylene imines), poly(urethanes), poly(α,β-unsaturated carboxylic acids), poly(α,β-unsaturated carboxy lie acid derivatives), poly(vinyl esters of carboxylic acids), poly(vinyl halides), poly(vinyl alkyl ethers), poly(N-vinyl compounds), poly(vinyl ketones), poly(vinyl aldehydes) and any combination thereof.

13. The method of claim 1 wherein at least a portion of residual functional groups in the one or more bilayers is reacted with an amine, hydroxyl group, thiol group, or hydrazine group having the formula R—NH$_2$, R—OH, R—SH or R—NHNH$_2$, where R is a substituted or unsubstituted C$_1$ to C$_{20}$ alkyl group or a substituted or unsubstituted C$_2$ to C$_{20}$ alkenyl group.

14. The method of claim 1 wherein at least a portion of residual functional groups in the one or more bilayers is reacted with an amine selected from the group consisting of decylamine, propylamine, an amino sugar, amino alcohol, amino polyol, glucamine, dimethylaminopropylamine (DMAPA), and combinations thereof.

15. The method of claim 1 wherein the oil infused into the one or more bilayers is selected from the group consisting of a silicone oil, a vegetable oil, a mineral oil, a thermotropic liquid crystal, and combinations thereof.

16. The method of claim 1 wherein the multilayer film comprises one or more PVDMA/PEI bilayers, which are further functionalized with n-decylamine and wherein the one or more bilayers are infused with a silicone oil or an anisotropic thermotropic liquid crystal.

17. The method of claim 1 wherein the substrate is curved or irregularly shaped.

18. The method of claim 1 wherein the substrate is a container for containing liquids or gels, wherein the first polymer layer, second polymer layer, and oil are selected so that said liquid or gel has reduced adhesion to the container.

19. A slippery liquid-infused porous surface (SLIPS) multilayer film comprising:
a) a multilayer film comprising one or more bilayers, wherein each bilayer comprises a first polymer layer in contact with a second polymer layer, where the multilayer film has nanoscale or microscale porosity and at least a portion of the multilayer film is functionalized to be hydrophobic; and
b) a hydrophobic oil selected from the group consisting of a silicone oil, a vegetable oil, a mineral oil, a thermotropic liquid crystal, and combinations thereof, wherein said oil coats at least the functionalized portion of the multilayer film and said oil at least partially fills the pores of at least the functionalized portion of the multilayer film.

20. The multilayer film of claim 19 wherein the multilayer film comprises 10 or more bilayers.

21. The multilayer film of claim 19 wherein the first polymer layer comprises a functionalized azlactone having the formula:

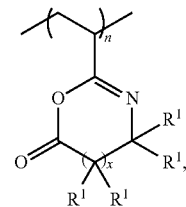

wherein x is 0 or the integers 1 or 2; and each R$^1$ is independently selected from the group consisting of: hydrogen, alkyl groups, alkenyl groups, alkynyl groups, carbocyclic groups, heterocyclic groups, aryl groups, heteroaryl groups, alkoxy groups, aldehyde groups, ether groups, and ester groups, any of which may be substituted or unsubstituted.

22. The multilayer film of claim 19 wherein the first polymer layer comprises a polymer selected from the group consisting of poly(vinyl-4,4-dimethylazlactone), poly(2-vinyl-4,4-dimethy1-2-oxazolin-5 -one), poly(2-isopropenyl-4,4-dimethyl-2-oxazolin-5-one), poly(2-viny1-4,4-diethy1-2-oxazolin-5-one), poly(2-vinyl-4-ethyl-4-methyl-2-oxazolin-5-one), poly(2-vinyl-4-dodecyl-4-methyl-2-oxazolin-5-one), poly(2-vinyl-4,4-pentamethy lene-2-oxazolin-5-one), poly (2-viny 1-4-methy 1-4-pheny 1-2-oxazolin -5 -one), poly(2-isopropenyl-4-benzyl-4-methyl-2-oxazolin-5-one), or poly(2-vinyl-4,4-dimethyl-1 ,3-oxazin-6-one).

23. The multilayer film of claim 19 wherein the second polymer layer comprises a primary amine functionalized polymer, an alcohol functionalized polymer, or a thiol functionalized polymer.

24. The multilayer film of claim 19 wherein the second polymer layer comprises an optionally functionalized polymer selected from the group consisting of polyolefins, poly(alkyls), poly(alkenyls), poly(ethers), poly(esters), poly(mides), polyamides, poly(aryls), poly(heterocycles), poly(ethylene imines), poly(urethanes), poly(α,β-unsaturated carboxylic acids), poly(α,β-unsaturated carboxy lie acid derivatives), poly(vinyl esters of carboxylic acids), poly(vinyl halides), poly(vinyl alkyl ethers), poly(N-vinyl compounds), poly(vinyl ketones), poly(vinyl aldehydes) and any combination thereof.

25. The multilayer film of claim 19 wherein at least a portion of residual functional groups in the one or more bilayers is reacted with an amine selected from the group consisting of decylamine, propylamine, an amino sugar, amino alcohol, amino polyol, glucamine, dimethylaminopropylamine (DMAPA), and combinations thereof.

26. The multilayer film of claim 19 comprising one or more PVDMA/PEI bilayers, which are further functionalized with n-decylamine and wherein the one or more bilayers are infused with a silicone oil or an anisotropic thermotropic liquid crystal.

27. A method for detecting an analyte, substance, or impurity in a liquid comprising the steps of:
 a) providing a sensor having a first surface area comprising:
  i) a multilayer polymer film comprising one or more bilayers, wherein each bilayer comprises a first polymer layer in contact with a second polymer layer, where said multilayer polymer film has nanoscale or microscale porosity and at least a portion of the multilayer film is functionalized to be hydrophobic; and
  ii) a hydrophobic oil selected from the group consisting of a silicone oil, a vegetable oil, a mineral oil, a thermotropic liquid crystal, and combinations thereof, wherein said oil coats at least the functionalized portion of the multilayer polymer film and said oil at least partially fills the pores of at least the functionalized portion of said multilayer polymer film;
 wherein said oil infused multilayer film exhibits a hydrophobic effect on said liquid;
 b) providing said liquid to said first surface area;
 c) comparing the adhesion of said liquid to said first surface area to a control sample or known standard of said liquid, wherein a change in the adhesion of said liquid to said first surface area indicates an analyte, substance, or impurity in said liquid.

28. The method of claim 27 wherein the first surface area comprises one or more optionally functionalized PVDMA/PEI bilayers and said oil is a thermotropic liquid crystal.

29. The method of claim 27 wherein the analyte, substance, or impurity is a bacterial endotoxin.

30. The method of claim 27 wherein comparing the adhesion of said liquid to said first surface area comprises comparing the time said liquid travels across said first surface area.

31. The multilayer film of claim 19 wherein the multilayer film has microscale porosity which is less than 100 μm.

32. The multilayer film of claim 19 wherein at least a portion of residual functional groups in the bilayer is reacted to form chemically labile amide/ester-, amide/thioester-, and amide/imine-type bonds.

* * * * *